(12) United States Patent
Voigt et al.

(10) Patent No.: US 12,262,866 B2
(45) Date of Patent: Apr. 1, 2025

(54) VISUALIZATION SYSTEM COMPRISING AN OBSERVATION APPARATUS AND AN ENDOSCOPE

(71) Applicant: Carl Zeiss Meditec AG, Jena (DE)

(72) Inventors: Christian Voigt, Abtsgmuend (DE); Stefan Saur, Aalen (DE); Christoph Hauger, Aalen (DE); Martin Fanenbruck, Oberkochen (DE); Helge Jess, Oberkochen (DE); Roland Guckler, Ulm (DE)

(73) Assignee: Carl Zeiss Meditec AG, Jena (DE)

( * ) Notice: Subject to any disclaimer, the term of this patent is extended or adjusted under 35 U.S.C. 154(b) by 631 days.

(21) Appl. No.: 17/508,865

(22) Filed: Oct. 22, 2021

(65) Prior Publication Data

US 2022/0079415 A1    Mar. 17, 2022

Related U.S. Application Data

(63) Continuation-in-part of application No. 16/139,032, filed on Sep. 22, 2018, now abandoned.

(30) Foreign Application Priority Data

Sep. 22, 2017  (DE) .................... 10 2017 216 853.6
Nov. 6, 2017   (DE) .................... 10 2017 219 621.1

(51) Int. Cl.
*A61B 1/00*   (2006.01)
*G06T 7/00*   (2017.01)
*G06T 7/30*   (2017.01)

(52) U.S. Cl.
CPC ........ *A61B 1/0005* (2013.01); *A61B 1/00006* (2013.01); *A61B 1/00183* (2013.01);
(Continued)

(58) Field of Classification Search
None
See application file for complete search history.

(56) References Cited

U.S. PATENT DOCUMENTS 10,413,159 B2 *   9/2019   Steffen ................. G02B 21/361
11,135,020 B2 *  10/2021   Enoki .................... A61B 1/313
(Continued)

FOREIGN PATENT DOCUMENTS

WO    2009128055 A1    10/2009

OTHER PUBLICATIONS

Office Action issued in German Patent Application No. DE 10 2017 219 621.1 (from which this application claims priority), dated May 2, 2018 and English language machine translation thereof.
(Continued)

*Primary Examiner* — John P Leubecker
(74) *Attorney, Agent, or Firm* — Ewers IP Law PLLC; Falk Ewers

(57) ABSTRACT

A visualization system includes an observation apparatus having a first image recording device to observe an operation region with a first observation plane, and an endoscope having a probe and a second image recording device to observe the operation region with a second observation plane. A display device represents a first image recorded by the first image recording device in a first orientation and a second image recorded by the second image recording device in a second orientation. The visualization system further includes a tracking system to determine an orientation of the endoscope relative to the observation apparatus and a controller configured to transform the second image based on the orientation of the endoscope relative to the observation apparatus.

17 Claims, 11 Drawing Sheets

(52) U.S. Cl.
CPC .............. *G06T 7/0012* (2013.01); *G06T 7/30* (2017.01); *G06T 2207/10068* (2013.01); *G06T 2207/20081* (2013.01); *G06T 2207/30004* (2013.01)

(56) References Cited

U.S. PATENT DOCUMENTS

| | | |
|---|---|---|
| 2001/0055062 A1 | 12/2001 | Shioda et al. |
| 2003/0069471 A1* | 4/2003 | Nakanishi ............ A61B 1/0005 600/101 |
| 2008/0262297 A1 | 10/2008 | Gilboa et al. |
| 2010/0249506 A1 | 9/2010 | Prisco |
| 2015/0250387 A1 | 9/2015 | Hauger et al. |
| 2015/0272694 A1* | 10/2015 | Charles ................. G16H 40/63 600/202 |
| 2015/0297311 A1* | 10/2015 | Tesar ................. G02B 21/0012 600/109 |
| 2016/0357003 A1* | 12/2016 | Hauger ................. G02B 21/361 |
| 2018/0256008 A1* | 9/2018 | Nishizawa ............... A61B 1/05 |
| 2019/0090728 A1* | 3/2019 | Fanenbruck ............ A61B 1/05 |
| 2019/0274518 A1* | 9/2019 | Themelis ............... A61B 8/12 |
| 2019/0328481 A1* | 10/2019 | Kamikawa ............ G16H 30/20 |

OTHER PUBLICATIONS

Hartley et al., "Multiple View Geometry in Computer Vision Second Edition", (2004), ISBN-13 978-0-521-54051-3, www.cambridge.org/9780521540513, Published by Cambridge University Press, New York, U.S.A.

* cited by examiner

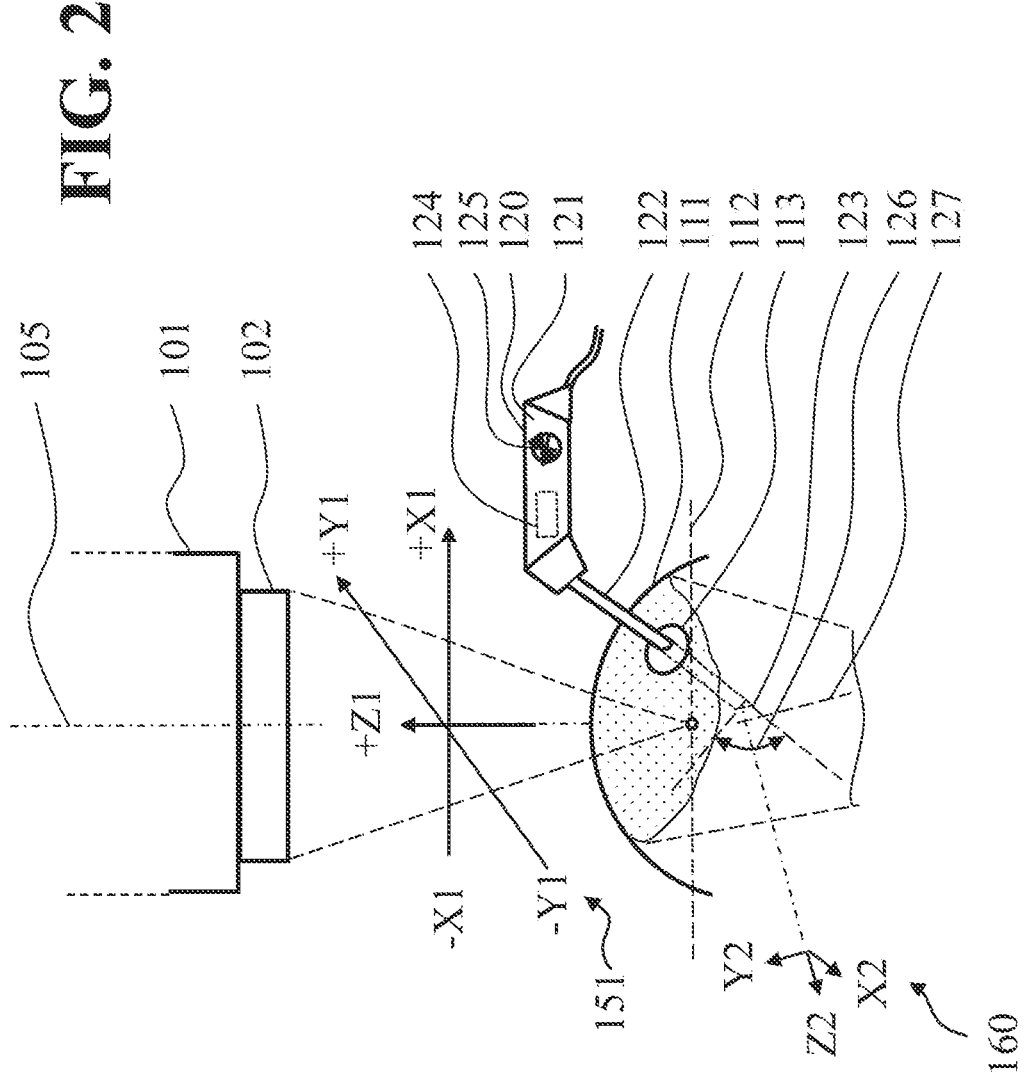
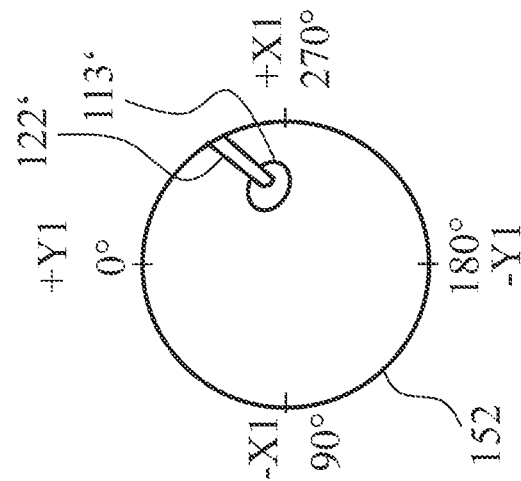
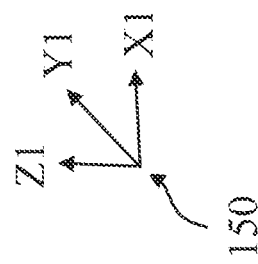
FIG. 2

VISUALIZATION SYSTEM COMPRISING AN OBSERVATION APPARATUS AND AN ENDOSCOPE

CROSS REFERENCE TO RELATED APPLICATIONS

This application is a continuation-in-part of U.S. patent application Ser. No. 16/139,032 filed Sep. 22, 2018, which was subsequently abandoned, and which claims priority to German patent application DE 10 2017 216 853.6, filed Sep. 22, 2017, and to German patent application DE 10 2017 219 621.1, filed on Nov. 6, 2017, the entire contents of which are incorporated herein by reference.

TECHNICAL FIELD

The disclosure relates to a visualization system including an observation apparatus and an optical inspection tool, and in particular to a visualization system and a method for operating the optical inspection tool.

BACKGROUND

An optical inspection tool, such as an endoscope, is a visualization instrument that is used during an examination or during an operation on a patient. An endoscope includes a probe that can be introduced into body channels, in particular into narrow and deep operation channels or cavities, in order to be able to view anatomical structures or body tissue of an operation region. One particular field of use is neurosurgery.

An endoscope is a manually guided medical instrument and can be used in addition to the observation apparatus in different positions in order to look at structures that are hidden in the microscopic view. The probe tip can have a mechanical marking in order to indicate a viewing direction of the probe. As soon as the probe tip is hidden by a tissue structure, however, the viewing direction of the probe is no longer discernible to the surgeon. When the image generated by the endoscope is viewed on a display device, the coordination of the direction of movement of the probe by a observer's hand, i.e., the hand-eye coordination, is hampered if the viewing direction of the probe tip is not clearly discernible.

SUMMARY

Therefore, it is an object of the disclosure to provide a visualization system including an observation apparatus and an optical inspection tool for operating the optical inspection tool, e.g., an endoscope in which the alignment of a probe of the endoscope is discernible and the hand-eye coordination during the movement of the endoscope is improved.

The object is achieved by a visualization system including an observation apparatus and an optical inspection tool as described herein.

According to an aspect of the disclosure, a visualization system includes an observation apparatus having a first image recording device for observing an operation region with a first observation plane, wherein in the first observation plane, a viewing direction is defined by a first viewing axis $Y1$.

The visualization system includes an optical inspection tool having a probe and a second image recording device configured to observe the operation region with a second observation plane with a second viewing axis $Y2$.

The visualization system includes a display device, which represents a first image recorded by the first image recording device in a first orientation and a second image recorded by the second image recording device in a second orientation. A control unit is connected to the second image recording device and the display device.

The endoscope includes a motion sensor, which is connected to the control unit, an angular position of the probe of the endoscope in space being determinable by said motion sensor. The control unit is configured to the effect that an angular position of the probe of the endoscope relative to the first viewing axis $Y1$ is determinable by evaluation of the data of the motion sensor, such that the second orientation of the second image is alignable depending on an angular position of the probe relative to the first viewing axis $Y1$.

The visualization system includes an observation apparatus having a first image recording device and the optical inspection tool having a second image recording device, and also a display device and a control unit.

The observation apparatus is configured to observe an operation region in a first observation plane, wherein in the first observation plane, a viewing direction is defined by the first viewing axis $Y1$.

The observation apparatus can be an optical surgical microscope includes eyepieces and one or more cameras. The observation apparatus can also be formed by a digital image capture system comprising a camera and an optical unit. The surgical microscope can also be formed only by a camera.

The operation region is a tissue region to be operated on, which is also referred to as the operation site. A viewing direction is a direction of view of an observer viewing an observation plane. A viewing axis is a reference axis that defines the direction of view of the observer relative to the observation plane. Said reference axis can also be referred to as the "0°" axis. Relative to a coordinate system of the first observation plane that is defined by the orthogonal axes $X1$, $Y1$, and $Z1$, the first viewing axis is defined by the axis $Y1$. A first viewing direction defines the direction of view with respect to the first observation plane.

In this case, the observable region of the operation site is not restricted to the first observation plane. The observable operation region is a three-dimensional region. The first observation plane defines a plane that is defined by the observation optical unit of the observation apparatus. The observation optical unit of the observation apparatus can also sharply image a region above and below the first observation plane, said region being defined by the depth of focus.

The operation region is recorded by the first image recording device and displayed in a first image in a first orientation on the display device. The first image represented on the display device can be an individual image, a sequence of individual images at specific points in time or a video image, also in real time.

The orientation of an image defines the alignment of a displayed image on the display device at a specific rotation angle. To that end, the first image recorded by the first image recording device can be rotated on the display device by an angle perpendicular to the first observation plane, about the $Z1$ axis, in such a way that a specific region is arranged at the top on the display device. The first image can be displayed in a first orientation on the display device in such a way that that region of the image which lies on the positive side on the first viewing axis $Y1$ is arranged at the top. If an observer looks along the direction of the first viewing axis $Y1$, the image recorded by the first image recording device can be displayed on the display device directly, without a change in the first orientation, i.e., without rotation angle correction.

The endoscope comprises a probe that is arranged on a handpiece and is guided manually by an observer. A probe is a thin tube several centimeters in length which can be introduced into a tissue region or a tissue structure. The image captured at the probe tip, the distal end of the probe, is guided via optical waveguides to the second image recording device. The operation region observable by the probe in a second observation plane is captured by the second image recording device and represented as a second image in a second orientation on the display device. The second image can be an individual image, a sequence of individual images at specific points in time, or a video image.

The first observation plane and the second observation plane are different observation planes. These two observation planes can be arranged at an angle with respect to one another. The first image and the second image show different views of the operation region. The first image and the second image can each comprise individual images and/or video image sequences.

A control unit is connected to the second image recording device and the display device. The second image recording device of the endoscope is connected to the display device via the control unit, such that the recorded images can be computationally processed, rotated, and/or altered. For this purpose, the control unit can comprise an image processing unit. The control unit comprises information about the alignment of the first viewing axis Y1. This information can be stored as a fixed numerical value in the control device.

The control unit processes the images of the second image recording device and determines the position of the second viewing axis Y2 therefrom. The second viewing axis Y2 is a reference axis that defines a direction of view of the probe relative to the tissue region viewed in a second observation plane. The second viewing axis Y2 can be defined by the geometric and optical construction of the endoscope. The second viewing axis Y2 can lie geometrically in the plane spanned by a center axis of the probe and of the handpiece of the probe. The second viewing axis Y2 can be identical to a mechanical marking of the probe tip, for example a jumper. The second viewing axis Y2 can also be manually adapted to an observer. By way of example, an observer who guides the endoscope using the left hand may have the need to indicate the second viewing axis Y2 subjectively in a different second orientation than an observer who guides the endoscope using the right hand. The observer can set the image to the observer's movement coordination by rotating the second viewing axis Y2 into a second orientation.

According to an aspect of the disclosure, the endoscope includes a motion sensor, which is connected to the control unit, an angular position of the probe of the endoscope in space being determinable by said motion sensor. The motion sensor is configured to capture a movement of the endoscope and to generate an electronically evaluatable movement value that can be evaluated by the control unit. A movement is characterized for example by a position change and/or an angular change of the endoscope in space. A movement can be uniform or comprise an acceleration. A movement can also be detected if it proves to be very small.

A motion sensor can capture a position change and/or an angular change in space. To that end, a motion sensor can for example be configured as a position sensor and determine an absolute angular position in space or determine a relative angular change with respect to a known angular position in space. As a result, an angular position of the probe in space is capturable. The angular position defines a rotation angle about one, two or three spatial axes, independently of the absolute 3D spatial coordinates.

The control unit is configured to the effect that an angular position of the probe of the endoscope relative to the first viewing axis Y1 is determinable by evaluation of the data of the motion sensor, such that the second orientation of the second image is alignable depending on an angular position of the probe relative to the first viewing axis Y1.

Once the probe of the endoscope has been introduced into a tissue region, the probe tip is no longer visible to the observer. The display device displays the image recorded by the second image recording device as a second image in a second orientation. The second orientation of the second image can be aligned in such a way that the second viewing axis Y2 is aligned in a relative position with respect to the first viewing axis Y1, said relative position being predefined by the control unit or the observer. The orientation of the second image with the second viewing axis Y2 of the endoscope can be adapted to the first orientation of the first viewing axis Y1 of the observation apparatus.

Upon a rotation of the probe about an axis, for example the longitudinal axis, without a tracking of the orientation of the second image, the second image would likewise be rotated on the display device.

The motion sensor arranged in the endoscope registers a movement of the endoscope. As a result of the angular position being determined by the motion sensor, the alignment of the probe with respect to the first viewing axis Y1 and with respect to the operation site is firstly captured and the alignment of the orientation of the second image is adapted. Upon a change in the position of the endoscope, the orientation of the second image can thus be tracked automatically. Consequently, an intuitive hand-eye coordination is advantageously possible for the observer who is manually guiding the endoscope.

Upon an alignment of the orientation of the second image with respect to the first viewing axis Y1, the second image is rotated on the display device in such a way that a direction of movement of the endoscope, for example in the direction of the first viewing axis Y1 of the microscope, is displayed as a movement on the display device in the second image in the same orientation as in the first image. The second orientation of the second image is alignable depending on an angular position of the probe relative to the first viewing axis Y1 and is trackable depending on the data of the motion sensor.

This shall be elucidated on the basis of an example. On a display device, the first image of the observation apparatus is oriented in such a way that the first viewing axis Y1 is displayed in a vertical direction. The probe of the endoscope is aligned in the direction of a surface normal with respect to the observation plane but rotated by 30° relative to the center axis of the probe.

On the display device, without this alignment, the second image would likewise be rotated by 30° with respect to the vertical relative to the first image. Upon a movement of the endoscope parallel to the first viewing axis Y1 of the microscope, the direction of movement in the second image would run obliquely by 30° with respect to the vertical direction relative to the first image. The observer's hand-eye coordination would be made more difficult.

Upon an alignment of the second orientation of the second image relative to the first viewing axis Y1, the rotation angle of the second image on the display device is corrected by 30° relative to the first image. Consequently, upon a movement of the endoscope parallel to the first viewing axis Y1 of the microscope, the direction of movement in the second image is represented in the same direction as in the first image. The observer who manually drives the endoscope, perceives this movement in the second image likewise in the vertical direction. This facilitates the hand-eye coordination for the observer. As a result of the angular position being determined by a motion sensor, the second orientation of the second image can be aligned and tracked depending on an angular position.

By way of example, the rotation of the wrist, which rotation would lead to a rotation of the second image on the display device, can be compensated for by a detection of the rotation angle by the motion sensor and a computational compensation by the control unit. If the observer rotates the endoscope about the center axis of the probe, for example when changing the position of the endoscope, the second orientation of the second image remains constant on the display device. The tracking of the orientation of the second image makes it possible to maintain the hand-eye movement coordination.

In one exemplary embodiment of the disclosure, a graphical marking is inserted in the second image represented on the display device, said graphical marking indicating the direction of the second viewing axis Y2 in the second image, wherein the graphical marking is trackable in the second image depending on an angular position of the probe relative to the first viewing axis Y1.

Once the probe of the endoscope has been introduced into a tissue region, the probe tip is no longer visible to the observer. In order to facilitate the handling of the endoscope for the observer and to make the orientation of the probe tip of the endoscope discernible to the observer, a graphical marking is inserted in the second image represented on the display device, said graphical marking indicating the direction of the second viewing axis Y2 in the second image. The control unit processes the images of the second image recording device and determines the position of the second viewing axis Y2 therefrom. The second viewing axis Y2 is inserted as a graphical marking into the second image represented on the display device. An alignment of the probe tip of the endoscope is thus discernible in the second image. The second image is displayed in a second orientation on the display device.

The control unit is configured to the effect that an angular position of the probe of the endoscope relative to the first viewing axis Y1 is determinable by evaluation of the data of the motion sensor, such that the graphical marking in the second image is trackable depending on an angular position of the probe relative to the first viewing axis Y1.

The display device displays the image recorded by the second image recording device as a second image together with the graphical marking. The graphical marking, indicating the second viewing axis Y2 of the endoscope, can be adapted to the first orientation of the first viewing axis Y1 of the observation apparatus. The observer who manually guides the endoscope can unambiguously assign the second viewing axis Y2 to the probe of the endoscope at any time by virtue of the marking in the second image.

Upon a rotation of the probe about an axis, for example the longitudinal axis, without a tracking, the graphical marking of the second viewing axis Y2 would likewise be rotated. The motion sensor arranged in the endoscope registers a movement of the endoscope. As a result of the angular position being determined by the motion sensor, the alignment of the probe with respect to the first viewing axis Y1 and with respect to the operation site is initially captured and indicated by the graphical marking in the second image. Upon a change in the position of the endoscope, the graphical marking can thus be tracked automatically. Consequently, an intuitive hand-eye coordination is advantageously possible for the observer who is manually guiding the endoscope.

In one exemplary embodiment of the disclosure, the control unit is connected to the first image recording device.

In this case, the control unit is connected to the first image recording device, the second image recording device, and the display device. The first image recording device of the observation apparatus and the second image recording device of the endoscope are connected to the display device via the control unit, such that the recorded images can be computationally processed and altered. For this purpose, the control unit can comprise an image processing unit.

In one exemplary embodiment of the disclosure, the viewing direction of the endoscope is formed at an angle relative to the center axis of the probe of the endoscope.

In this way, it is possible to view a tissue region situated laterally with respect to the probe. This is advantageous if the probe is introduced in a narrow channel.

In one exemplary embodiment of the disclosure, the motion sensor is a sensor selected from a position sensor, an acceleration sensor, a vibration gyroscope sensor, and a gyrosensor.

All these sensors are cost-effective and available in miniaturized form.

In one exemplary embodiment of the disclosure, the motion sensor is a position sensor. The position sensor can determine an angular position in space. The position sensor is configured to determine a relative inclination angle with respect to a perpendicular axis. An angular position can thus be determined independently of an acceleration. Position sensors are cost-effective.

In one exemplary embodiment of the disclosure, the motion sensor is an acceleration sensor. An acceleration sensor is cost-effective and available in miniaturized form. Moreover, an acceleration sensor has a high measurement accuracy.

In one exemplary embodiment of the disclosure, the motion sensor is a vibration gyroscope sensor.

Simple position sensors may be restricted to one axial direction, such that movements that take place perpendicular to this axial direction cannot be detected. If a position sensor detects a movement in a perpendicular direction on the basis of the gravitational force, for example, a rotational movement perpendicular to the gravitational force direction cannot be detected. In the case of an endoscope, this may have the disadvantage that in the event of a specific alignment of the axis of the probe, for example, movement in a perpendicular direction, a rotation about this axis cannot be perceived by the position sensor since no vertical component of the movement is present.

A vibration gyroscope sensor makes it possible to measure rotational movements. For this purpose, a vibration gyroscope sensor comprises at least one oscillatory system, for example a quartz oscillator. A vibration gyroscope sensor can comprise three quartz oscillators aligned orthogonally to one another. If a quartz oscillator is rotated perpendicular to the deflection direction $\alpha$ at the angular velocity $\omega$, the Coriolis force $F=d\alpha/dt*\omega$ acts perpendicular thereto on the oscillation system. The alteration can be detected by a piezoelectric pick-up, such that a rotational movement is determinable. Vibration gyroscope sensors can be made very small, for example on a microelectromechanical basis.

In one exemplary embodiment of the disclosure, the motion sensor is a gyrosensor.

A gyrosensor is a piezo-based acceleration or position sensor that can measure very small accelerations, rotational movements, or position changes. Advantageously, the gyrosensor can simultaneously detect the acceleration value and the inclination angle. As a result, a single sensor can form an acceleration sensor and the position sensor. Gyrosensors can be made very small and are cost-effective.

In one exemplary embodiment of the disclosure, the motion sensor is arranged in the handpiece.

There is enough space for the sensor in the handpiece. Moreover, the sensor can be arranged on an electronics circuit board already present in the handpiece. This saves additional signal lines or power supply lines for the sensor.

In one exemplary embodiment of the disclosure, the handpiece comprises a position sensor and an acceleration sensor.

Advantageously, the two sensors can synergistically complement one another.

In one exemplary embodiment of the disclosure, the second image recording device is fixedly connected to the probe.

This is the mechanically simple connection and thus cost-effective and compact. The endoscope can be calibrated in a simple manner.

In one exemplary embodiment of the disclosure, the second image recording device is arranged rotatably relative to the probe.

In this exemplary embodiment, the second image recording device is mounted rotatably relative to the optical unit of the probe. The recorded image can therefore be displayed directly on the display device. This reduces the computational complexity for image processing in the control unit and allows a faster image sequence on the display device.

In one exemplary embodiment of the disclosure, the control unit comprises an image processing unit.

An image processing unit can be formed for example by a specific computer chip or a graphics card that is optimized for fast image processing operations. It is thus possible to effect processing of the images and the insertion and/or tracking of the graphical marking particularly rapidly and in real time.

In one exemplary embodiment of the disclosure, at least two graphical markings are inserted in the second image on the display device.

In this way, two items of information can be made available to the observer; by way of example, a first graphical marking can correspond to a mechanical marking of the probe tip and a second graphical marking can indicate a direction selectable by the observer, or a center axis of the probe corresponding to a straight ahead view or advance direction of the probe. All graphical markings are trackable depending on the data of the motion sensor and thus on an angular position of the probe relative to the first viewing axis Y1.

In one exemplary embodiment of the disclosure, the alignment of the probe relative to the first observation plane is determinable by image evaluation of the images captured by the first image recording device.

At least one part of the probe is visible in the image captured by the first image recording device of the observation apparatus. The observation apparatus image is evaluatable by the control unit. An alignment of the probe relative to the first observation plane is thus determinable by evaluation of the image information of the first image recording device. This information about the alignment of the probe can be supplemented by the items of information provided by the motion sensor. The system can be calibrated on the basis of this information. Typically, the alignment of the probe relative to the first observation plane is already determinable before the first determination of an angular position by the motion sensor by image evaluation of the image captured by the first image recording device.

In one exemplary embodiment of the disclosure, the alignment of the probe relative to the first observation plane is tracked by a navigation system before the first determination of an angular position by the motion sensor.

Typically, an alignment of the probe with respect to the operation site can thus be determined beforehand and as a start value for a motion detection that follows by the motion sensor. The system can be calibrated by the navigation system after being switched-on, and an angular position and/or a position in space can be calculated.

In one exemplary embodiment of the disclosure, with an additional navigation system, a position and/or an alignment of the probe of the endoscope are/is determinable by tracking of a navigation element arranged on the endoscope.

A navigation system can already be part of the equipment of a surgical system or is additionally supplementable. Typically, this can be used to determine an absolute spatial position and/or angular position of the endoscope by a tracking element. The combination of navigation system and motion sensor enables the angular position of the endoscope to be determined very precisely. Typically, further surgical tools or the patient's body part to be operated on can be tracked by the navigation system.

In one exemplary embodiment of the disclosure, with an additional navigation system, an angular position of the probe of the endoscope is determinable by tracking of a navigation element arranged on the endoscope.

It may be sufficient to determine an angular position of the probe in space by a tracking element.

In one exemplary embodiment of the disclosure, the navigation system is formed by an electromagnetic tracking system having at least one transmitter and at least one receiver.

Electromagnetic tracking between the observation apparatus and the probe has the advantage over the conventional navigation solutions that no navigation elements, for example navigation image recording devices, having an adverse effect on visibility or handling, need to be mounted on the probe of the endoscope. By way of example, it would be necessary merely to accommodate an RFID chip or a solenoid in the handle of the endoscope or to mount it on the handle. Moreover, the distance from the observation apparatus, for example, a surgical microscope or a camera, and the endoscope is in a favorable range for electromagnetic tracking.

In one exemplary embodiment of the disclosure, at least two different images captured by the second image recording device of the endoscope at two different points in time are represented on the display device.

The display of two different images allows the representation of preoperative image data together with current image data. Moreover, two views can be represented at two different points in time. Alternatively, the display of an individual image together with a live video image is conceivable.

In one exemplary embodiment of the disclosure, the first image of the observation apparatus and the second image of the endoscope are displayed in a "Picture-In-Picture" representation on the display device.

A "Picture-In-Picture" representation is the display of the second image as an inserted sub-picture in the first image. For this purpose, the second image can be represented with reduced size or be represented only partly in an excerpt. As a result of the spatial proximity of the first image and the second image, the images can be registered visually more rapidly by a observer.

In one exemplary embodiment of the disclosure, a motion value is determinable by an analysis of the images provided by the second image recording device.

A second image recording device of the endoscope can record images in temporal succession. A motion value can be derived therefrom in the control unit, for example by image processing software. The image capture system thus forms an additional motion sensor that improves the motion detection and resolution of the overall system even further.

In one exemplary embodiment of the disclosure, the power supply of the endoscope is wire-free and comprises a battery or a rechargeable battery.

In the case of battery- or rechargeable-battery-operated medical apparatuses, it is possible to dispense with a connecting cable. As a result, the handling of the endoscope is simpler and more flexible since no cable needs to be carried along in the event of a change in the position of the endoscope.

In one exemplary embodiment of the disclosure, the observation apparatus is a surgical microscope.

Surgical microscopes can comprise image recording devices, for example, image recording sensors or cameras. A digital surgical microscope can be formed by a camera having an optical unit. Typically, an endoscope can be retrofitted to supplement an already existing surgical microscope.

In one exemplary embodiment of the disclosure, the observation apparatus is a camera.

A camera is compact and cost-effective and scarcely impedes an observer during an examination or operation.

According to another aspect of the disclosure, the visualization system for operating the optical inspection tool includes an observation apparatus having a first image recording device configured to observe an operation region at a first observation plane, the first observation plane having a first observation plane axis and a second observation plane axis and defining a first viewing axis which is perpendicular to the first plane axis and the second plane axis.

The optical inspection tool has a second image recording device configured to observe the operation region at a second observation plane, and the second observation plane has a third plane axis and a fourth plane axis and defines a second viewing axis which is perpendicular to the third plane axis and the fourth plane axis.

The visualization system according to this aspect of the disclosure further includes a display device configured to represent a first image recorded by the first image recording device and a second image recorded by the second image recording device.

In addition, a tracking system is provided which includes a target detection device and at least one target. The tracking system is configured to determine an orientation of the optical inspection tool relative to the observation apparatus.

Further, the visualization system according to this aspect of the disclosure includes a controller with a memory and a processor in communication with the first image recording device, the second image recording device, the tracking system, and the memory. The processor is configured to transform the second image based on the orientation of the optical inspection tool relative to the observation apparatus.

According to an exemplary embodiment of the disclosure, to transform the second image, the processor is further configured to generate a projected observation plane by projecting the second observation plane onto the first observation plane, wherein the projected observation plane has a projected third plane axis and a projected fourth plane axis and defines a projected second viewing axis which is aligned perpendicular to the projected third plane axis and the projected fourth plane axis, and wherein the projected third plane axis, the projected fourth plane axis, and the projected second viewing axis define a projected coordinate system.

The processor is further configured to determine a rotation angle which indicates a rotation of the projected coordinate system about the projected second viewing axis such that the projected third plane axis is aligned parallel to and equally oriented with the first plane axis, and the projected fourth plane axis is aligned parallel to and equally oriented with the second plane axis, and to rotate the second image about the rotation angle.

According to an exemplary embodiment of the disclosure, to transform the second image, the processor is further configured to define a reference plane. The reference plane is defined as a plane having a first reference plane axis and a second reference plane axis, and the first and second reference plane axes are aligned perpendicular to the gravitation or gravitational force.

According to yet another exemplary embodiment of the disclosure, to transform the second image, the processor is further configured to generate a projected first observation plane by projecting the first observation plane onto the reference plane, wherein the projected first observation plane has a projected first plane axis and a projected second plane axis and defines a projected first viewing axis.

When the second viewing axis is aligned perpendicular to the reference plane, the processor is configured to determine a first rotation angle $\alpha_1$ and to rotate the second image about the first rotation angle $\alpha_1$ such that a rotated third plane axis of the rotated second observation plane is aligned parallel to and equally oriented with the projected first plane axis, and the projected fourth plane axis is aligned parallel to and equally oriented with the second plane axis.

According to another exemplary embodiment of the disclosure, to transform the second image, the processor is further configured to define a horizontal plane and a vertical plane. The horizontal plane is aligned parallel to and equally oriented with the reference plane and the vertical plane is aligned perpendicular to the reference plane. The processor is further configured to generate a projected horizontal observation plane by projecting the second observation plane onto the horizontal plane and a projected vertical observation plane by projecting the second observation plane onto the vertical observation plane, to determine a first rotation angle $\alpha_1$ such that a rotated projected third plane axis of the projected horizontal observation plane is aligned parallel to and equally oriented with the projected first plane axis, to determine a second rotation angle $\alpha_2$ such that a rotated projected fourth plane axis of the projected vertical observation plane is directed away from and perpendicular to the reference plane in a direction opposite to the gravitation, to determine a tilt angle $\beta$ relative to the reference plane, to determine a third rotation angle $\alpha_3$ based on the first rotation angle $\alpha_1$, the second rotation angle $\alpha_2$, and the tilt angle $\beta$, and to rotate the second image about the third rotation angle $\alpha_3$ about the projected second viewing axis. The third rotation angle $\alpha_3$ is determined in accordance with $$\alpha_3 = g(\beta) \cdot \alpha_1 + (1 - g(\beta)) \cdot \alpha_2$$

wherein $\alpha_1$ is the first rotation angle, $\alpha_2$ is the second rotation angle, and $g(\beta)$ is a function of the tilt angle $\beta$.

According to an exemplary embodiment of the disclosure, a value of a function $g(\beta)$ of the tilt angle $\beta$ is 0 when the tilt angle $\beta$ is 0°, the value of the function $g(\beta)$ of the tilt angle $\beta$ is 1 when the tilt angle $\beta$ is 90°, the function $g(\beta)$ of the tilt angle $\beta$ is monotonically increasing, and the function $g(\beta)$ of the tilt angle $\beta$ is adjustable.

According to yet another exemplary embodiment of the disclosure, the observation apparatus is a microscope, the optical inspection tool is an endoscope, the target detection device is a camera, and the at least one target is a marker.

According to an exemplary embodiment of the disclosure, to transform the second image, the processor is further configured to define a vertical axis of the second image, and to reflect or mirror the second image on the vertical axis. The mirroring is performed when the first viewing axis Y1 and the second viewing axis Y2 are oriented opposite to one another. This is the case, for example, when there is an angle of more than 90° between Y1 and Y2 or when the scalar product of the normalized vector Y1 and the normalized vector Y2 is negative.

According to a further exemplary embodiment of the disclosure, the second image is transformed relative to the first image by training the visualization system. To transform the second image by training, the second image is repeatedly manually rotated about the projected second viewing axis corresponding to a rotation angle depending on the orientation of the optical inspection tool relative to the observation apparatus, and the processor is further configured to store values of the rotation angle in a training database each time the second image is rotated about the rotation angle, to compare the values previously stored in the training database with the values subsequently stored in the training database, and to automatically rotate the second image about the rotation angle based on the training of the visualization system.

According to a further aspect of the disclosure, a method for operating an optical inspection tool is provided. The method includes observing, with an observation apparatus, an operation region at the first observation plane, the first observation plane having a first plane axis and a second plane axis and defining a first viewing axis which is aligned perpendicular to the first plane axis and the second plane axis, observing, with the optical inspection tool, the operation region at the second observation plane, the second observation plane having a third plane axis and a fourth plane axis and defining a second viewing axis which is aligned perpendicular to the third plane axis and the fourth plane axis, and determining, with a tracking system, an orientation of the optical inspection tool relative to the observation apparatus, and transforming the second image relative to the first image based on the orientation of the optical inspection tool.

According to this aspect of the disclosure, the method further includes transforming the second image relative to the first image includes generating a projected observation plane by projecting the second observation plane onto the first observation plane, wherein the projected observation plane has a projected third plane axis and a projected fourth plane axis and defining a projected second viewing axis which is aligned perpendicular to the projected third plane axis and the projected fourth plane axis, and wherein the projected third plane axis, the projected fourth plane axis, and projected second viewing axis define a projected coordinate system, determining a rotation angle which indicates a rotation of the projected coordinate system about the projected second viewing axis such that the projected third plane axis is aligned parallel to and equally oriented with the first plane axis, and the projected fourth plane axis is aligned parallel to and equally oriented with the second plane axis; and rotating the second image about the rotation angle.

According to an exemplary embodiment of the disclosure, transforming the second image relative to the first image includes defining a reference plane. The reference plane is a plane having a first reference plane axis and a second reference plane axis, and the first and second reference plane axes are aligned perpendicular to the gravitation or gravitational force.

According to another exemplary embodiment of the disclosure, the method of transforming the second image includes generating a projected first observation plane by projecting the first observation plane onto the reference plane, wherein the projected first observation plane has a projected first plane axis and a projected second plane axis and defines a projected first viewing axis, and when the second viewing axis is aligned perpendicular to the reference plane, determining a first rotation angle $\alpha_1$ and rotating the second image about the first rotation angle $\alpha_1$ such that a rotated third plane axis of the rotated second observation plane is aligned parallel to and equally oriented with the projected first plane axis, and the projected fourth plane axis is aligned parallel to and equally oriented with the second plane axis.

According to another exemplary embodiment of the disclosure, transforming the second image includes defining a horizontal plane and a vertical plane, wherein the horizontal plane is aligned parallel to and equally oriented with the reference plane and the vertical plane is aligned perpendicular to the reference plane, generating a projected horizontal observation plane by projecting the second observation plane onto the horizontal plane and generating a projected vertical observation plane by projecting the second observation plane onto the vertical observation plane, determining a first rotation angle $\alpha_1$ such that a rotated projected third plane axis of the projected horizontal observation plane is aligned parallel to and equally oriented with the projected first plane axis, determining a second rotation angle $\alpha_2$ such that a rotated projected fourth plane axis of the projected vertical observation plane is directed away from and perpendicular to the reference plane in a direction opposite to the gravitation, determining a tilt angle $\beta$ relative to the reference plane, determining a third rotation angle $\alpha_3$ based on the first rotation angle $\alpha_1$, the second rotation angle $\alpha_2$, and the tilt angle $\beta$, and rotating the second image about the third rotation angle $\alpha_3$ about the projected second viewing axis.

According to an exemplary embodiment of the disclosure, the third rotation angle $\alpha_3$ is determined in accordance with $$\alpha_3 = g(\beta)\cdot\alpha_1 + (1-g(\beta))\cdot\alpha_2$$

wherein $\alpha_1$ is the first rotation angle, $\alpha_2$ is the second rotation angle, and $g(\beta)$ is a function of the tilt angle $\beta$.

According to an exemplary embodiment of the disclosure, a value of a function $g(\beta)$ of the tilt angle $\beta$ is 0 when the tilt angle $\beta$ is 0°, the value of the function $g(\beta)$ of the tilt angle $\beta$ is 1 when the tilt angle $\beta$ is 90°, the function $g(\beta)$ of the tilt angle $\beta$ is monotonically increasing, and the function $g(\beta)$ of the tilt angle $\beta$ is adjustable.

According to another exemplary embodiment of the disclosure, the observation apparatus is a microscope, the optical inspection tool is an endoscope, the target detection device is a camera, and the at least one target is a marker.

According to an exemplary embodiment of the disclosure, transforming the second image relative to the first image includes defining a vertical axis of the second image, and reflecting the second image on the vertical axis.

Another exemplary embodiment of the disclosure includes transforming the second image relative to the first image by training the visualization system. To transform the second image by training, the method includes repeatedly manually rotating the second image about the projected second viewing axis corresponding to a rotation angle depending on the orientation of the optical inspection tool relative to the observation apparatus, storing values of the rotation angle in a training database each time the second image is rotated about the rotation angle, comparing the values previously stored in the training database with the values subsequently stored in the training database, and automatically rotating the second image about the rotation angle based on the training of the visualization system.

BRIEF DESCRIPTION OF THE DRAWINGS

The disclosure will now be described with reference to the drawings wherein:

FIG. 2 shows an enlarged excerpt from the operation scenario in accordance with FIG. 1 with a first coordinate system;

DESCRIPTION OF EXEMPLARY EMBODIMENTS

Figure 1:
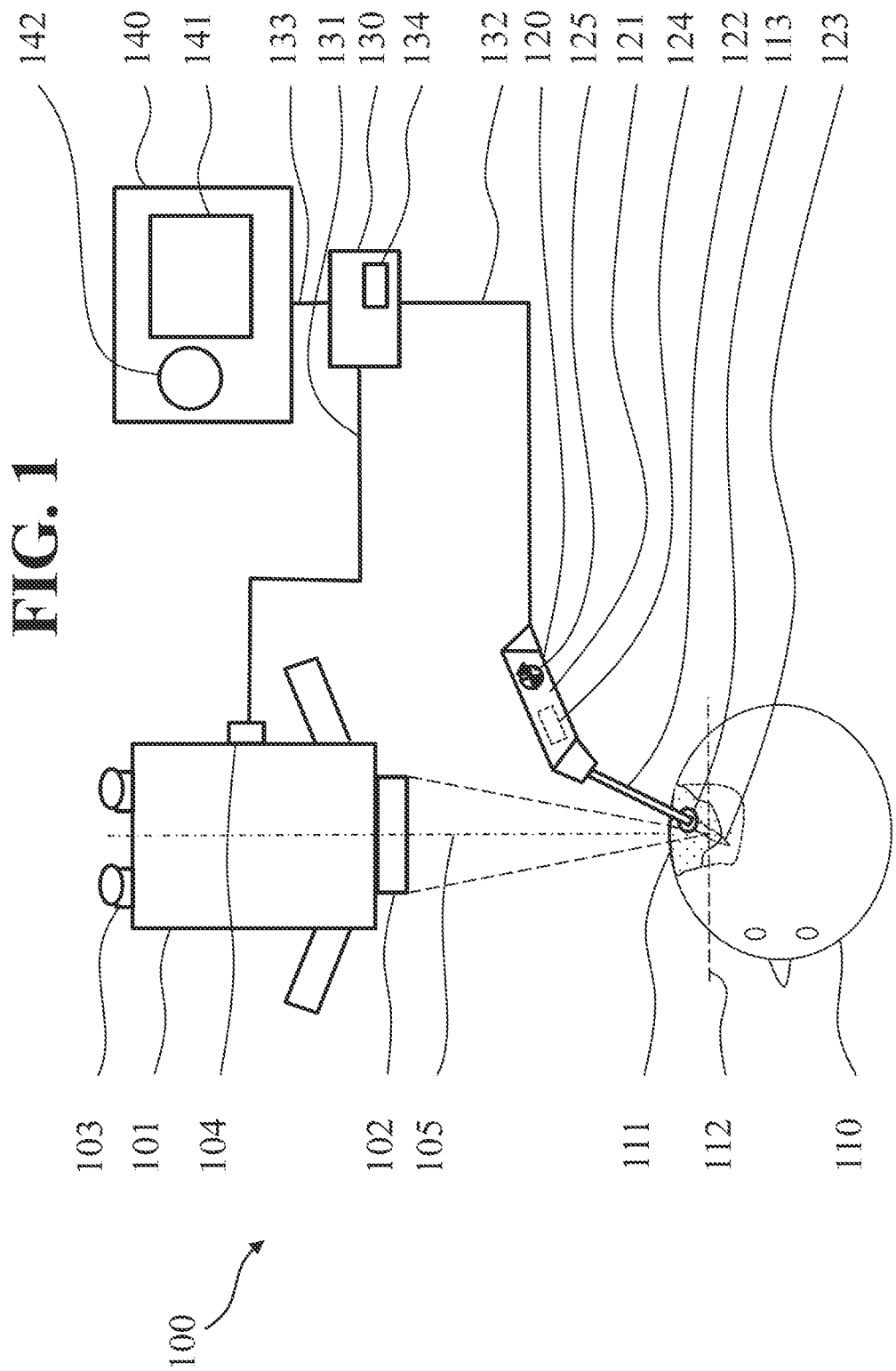
FIG. 1 shows an observation apparatus and an endoscope in an operation scenario according to a first exemplary embodiment of the disclosure.

FIG. 1 shows an observation apparatus and an endoscope 120 in an operation scenario 100 according to a first exemplary embodiment of the disclosure.

The observation apparatus is a surgical microscope 101. The surgical microscope 101 having a main objective 102 is represented for the observation of an object 110 to be observed, for example a patient's head. The main objective 102 has an optical axis 105. The surgical microscope is configured as a stereo microscope. An observer or surgeon can view an operation region 111 with an object plane, which is referred to as first observation plane 112, through the eyepieces 103. The surgical microscope 101 comprises a first image recording device 104. The image recording device 104 captures an image or a video sequence of the operation region 111.

The tissue to be operated on in the operation region 111 is additionally observed via the endoscope 120. The endoscope 120 comprises a handpiece 121 and a probe 122. The handpiece 121 is arranged in an angled manner relative to the probe; the angle is 45°, for example. Grip surfaces (not illustrated) can be mounted on the exterior of the handpiece 121. A second image recording device 124, depicted by dashed lines, a motion sensor 125, an illumination device (not illustrated), and an interface for data communication are arranged in the interior of the handpiece 121.

The probe 122 comprises a long thin tube having a probe tip 123. The probe tip 123 defines the distal end of the probe 122. The probe 122 is introduced into the tissue in the operation region 111 via a body opening 113 in order to view anatomical structures or body tissue behind the first observation plane 112. An optical unit (not illustrated) is arranged on the probe tip 123. The probe 122 comprises a first optical waveguide for illuminating a tissue region and a second optical waveguide, which is led from the optical unit on the probe tip 123 to the second image recording device 124. In one exemplary embodiment, the optical waveguide can also be formed by an electron conductor. In one exemplary embodiment, the image capture device can also be arranged on the probe tip 123.

The first image recording device 104 is connected to a control unit 130 via first line 131. The endoscope 120 is connected to the control unit 130 by a second line 132. The control unit 130 comprises an image processing unit 134. The control unit 130 is coupled to a display device 140 via a third line 133. The display device 140 shows the image captured by the first image recording device 104 of the surgical microscope 101 in a first image 141. The image captured by the second image recording device 124 of the endoscope 120 is represented in a second image 142 on the display device 140.

The images captured by the first image recording device 104 of the surgical microscope 101 or the second image recording device 124 of the endoscope 120 can in each case represent individual images or video sequences.

The surgical microscope 101 can be a conventional optical stereo surgical microscope, wherein the observation region can be viewed through the eyepieces 103. The surgical microscope 101 can also be configured as a purely digital surgical microscope, wherein the operation region 111 with the first observation plane 112 is recorded by the first image recording device 104 and represented on the display device 140. The surgical microscope 101 can also be configured as a hybrid system and both enable an observation through eyepieces 103 and have one or more first image recording devices 104 for representing the observation region with the first observation plane 112. The surgical microscope 101 can also be formed by a single camera. The first image 141 of the first image recording device 104 of the surgical microscope 101, said first image being represented on the display device 140, can be displayed as a two- or three-dimensional image.

The endoscope 120 can furthermore have an energy store for power supply independent of the electricity grid, for example a battery or a rechargeable battery or a capacitor having a very large capacitance. The endoscope 120 is hermetically encapsulated. The endoscope is fully autoclavable. In use during an operation, however, the endoscope 120 can also be protected by a sterile protective film, referred to as a drape.

The control unit 130 is formed by a microcontroller assembly or an industrial computer, for example. The image processing unit 134 is part of the control unit 130 and comprises a hardware and/or a software module. The control unit 130 can be integrated into the surgical microscope 101 or in the display device 140. The control unit 130 can also be divided into a plurality of assemblies. An assembly of the control unit 130 can be integrated into the endoscope 120. The first line 131, the second line 132 and the third line 133 can be formed in wired or wireless fashion. A wired line can be a network line or a data line, for example a coaxial cable or a fiber-optic cable. A wireless connection can be formed by radio, WLAN or Bluetooth® and in each case comprise a transceiver unit.

The first image recording device 104 of the surgical microscope 101 or the second image recording device 124 of the endoscope 120 can be in each case a camera or an image sensor, for example a charge-coupled device (CCD) chip. An image recording device can record monochrome images and/or color images. An image recording device can also be configured to record fluorescence images. One or a plurality of optical elements (not illustrated), for example lenses, stops, or filters, can be arranged upstream of the image sensor. An image recording device can comprise a single image sensor or a plurality of image sensors and can be configured to record 2D or 3D images. An endoscope 120 can also be an ultrasonic probe.

The display device 140 is a screen, which can be configured as a 2D screen or a 3D screen. In an exemplary embodiment, the display device 140 is a data projection device in the surgical microscope 101. A data projection device is a display device whose image is inserted into one or both observation beam paths of the surgical microscope 101. A data projection device can represent a monochrome image or a colored image. The data projection device can represent the image recorded by the second image recording device 124 of the endoscope 120 together with additional information. Additional information can be preoperative images or text information, for example. A 2D screen or a 3D screen can also be present together with the data projection device.

If the display device 140 is a screen, the images of the first image recording device 104 of the surgical microscope 101 and of the second image recording device 124 of the endoscope 120 can be displayed together. In this case, the second image 142, the endoscope image, can be represented as a sub-picture in the first image 141 captured by the surgical microscope. This is referred to as "Picture-in-Picture" representation.

In an exemplary embodiment, the first line 131 is led from the first image recording device 104 directly to the display unit 140. For this purpose, the first line 131 can also be led through the control unit 130, without being connected to the image processing unit 134. The control unit can comprise information about the alignment of the first viewing axis Y1. This information can be stored as a fixed value in the control device.

FIG. 2 shows an enlarged excerpt from the operation scenario in accordance with FIG. 1 with a first coordinate system 150.

The first coordinate system 150 comprises the orthogonal axes X1, Y1, and Z1. The first coordinate system 150 is additionally represented below the main objective 102, perpendicular to the optical axis 105, and is identified by the reference sign 151. Said first coordinate system 150 is also defined for the first observation plane 112. The axis Z1 is formed by the optical axis 105. The observer (not illustrated) is situated at a position in front of the operation region 111 and looks from a direction −Y1 in the direction +Y1. This direction of view defines the first viewing direction of the observer relative to the surgical microscope. This first viewing direction is the "0°" viewing direction for the observer. The axis Y1 forms the first viewing axis. The X1-axis is defined orthogonally to the axis Y1. From the observer's viewpoint, the −X1-axis segment is defined as left, and the +X1-axis segment is defined as right.

A surgical microscope image 152 shows a representation of the image that can be viewed through the surgical microscope 101. The surgical microscope image 152 can be viewed through the eyepieces 103. In addition, the surgical microscope image 152 is recorded by the first image recording device 104 and can be displayed as a first image 141 on the display device 140, as shown in FIG. 1. The X1-axis runs from left to right. The axis Y1, defining the first viewing direction of the observer, runs from bottom to top. The first viewing direction "0°" defined for the observer is marked at the top in the surgical microscope image 152.

The surgical microscope image 152 shows the operation region 111 to be observed. Moreover, part of the probe 122 is visible, which is designated by the reference sign 122'.

The probe 122 is introduced into the tissue in the operation region 111 via the body opening 113, designated by the reference sign 113'. The probe tip 123 of the probe 122 is not visible in the surgical microscope image 152.

An optical unit, configured as a wide-angled optical unit, is arranged on the probe tip 123 of the endoscope 120, such that the direction of view of the probe tip 123 is not implemented in an extension of the center axis of the probe 122, but rather at an angle with respect to the center axis thereof. Said angle is approximately 45°, relative to the center axis of the probe 122. The wide-angle optical unit arranged on the probe tip 123 brings about an enlarged aperture angle 126. The aperture angle 126 of the wide-angle optical unit is 100° in this exemplary embodiment. In addition, the handpiece 121 is angled by a specific angle relative to the probe 122. Said angle is 45°, for example.

In an exemplary embodiment, the probe tip can also be configured in a different shape and have a different direction of view and a different aperture angle.

The second image recording device 124 of the endoscope 120 can record an image of anatomical structures below the first observation plane 112 from a lateral direction in a second observation plane 127. The second observation plane 127 differs from the first observation plane 112. The first observation plane 112 and the second observation plane 127 are arranged at an angle with respect to one another. Said angle is 80°, for example. The image recorded by the second image recording device 124 is referred to as endoscope image. The endoscope image defines a second coordinate system 160 having the orthogonal axes X2, Y2 and Z2.

The second viewing direction of the probe 122 is defined by the geometric and optical construction of the endoscope 120. In this exemplary embodiment, the second viewing direction of the probe 122 is defined by the Y2-axis. The Y2-axis lies in the plane spanned by the center axis (not illustrated) of the probe 112 and of the handpiece 125. The Y2-axis forms the second viewing axis.

In the endoscope image, the midpoint of the second observation plane 127 lies at the center of the observation cone spanned by the wide-angle optical unit. In FIG. 2, the midpoint of the endoscope image is marked as rearward extension of the Z2-axis of the second coordinate system 160. Therefore, the midpoint of the endoscope image does not lie in an extension of the center axis of the probe 122, where the observer would intuitively expect the midpoint. In the endoscope image, the region which lies in the extension of the center axis of the probe 122 is represented at the image edge, in the negative region of the Y2-axis, as it were in a 180° position.

For the observer who manually guides the endoscope 120, this angled configuration poses a certain challenge for hand-eye coordination. This is additionally made more difficult since the probe tip 123 in the operation channel lying in the tissue in the operation region 111 below the body opening 113 is not visible to the observer either with the naked eye or with the surgical microscope 101.

The anatomical structure to be viewed in the surgical microscope, for example an aneurysm, hides part of the probe 122 and the probe tip 123. Moreover, the probe tip 123 may be particularly close to tissue to be dealt with carefully or a structure to be dealt with carefully. An erroneous movement of the probe 122 in the axial direction of the center axis of the probe 122, deeper into the operation channel in the advance direction, might bring about undesired tissue damage.

Therefore, a graphical marking is inserted in the second image 142, the endoscope image, represented on the display device 140, said graphical marking indicating the direction of the second viewing axis Y2 in the second image.

In one exemplary embodiment, the second image 142 represented on the display device 140 is rotated in such a way that the second viewing axis Y2 corresponds to the first viewing axis Y1. In this exemplary embodiment, the second image 142 is rotated by an angle in such a way that the second viewing axis Y2 is arranged vertically. The image region lying in the Y2-direction is displayed at the top.

In one exemplary embodiment, the image rotation of the second image 142 is carried out together with the display of the graphical marking.

In another exemplary embodiment, the graphical marking can also mark an image region which displays a straight ahead view in the advance direction of the probe 122. In this exemplary embodiment, the advance direction lies in a 180° position, i.e., in the vicinity of the lower image edge of the second image 142.

All the variants mentioned above can be present individually or in combination. It is conceivable for two graphical markings to mark a viewing axis Y2 and an advance direction and additionally for the second image to be represented in a manner rotated by an angle on the display device 140.

It is also conceivable for the image rotation of the second image 142 to be carried out without a display of the graphical marking. By way of example, the second image 142 is rotated by an angle in such a way that the second viewing axis Y2 is arranged vertically. The image region lying in the Y2-direction is displayed at the top. In this exemplary embodiment, a display of the graphical marking can be dispensed with.

The rotation of the second image and/or a graphical marking make(s) possible for the observer a reliable orientation in the second image 142 represented on the display device 140 and an unambiguous assignment of the tissue region lying in the advance direction of the probe 122 and thus significantly facilitate(s) hand-eye coordination.

The surgical microscope image 152 shows a part of the probe 122'. The surgical microscope image 152 is evaluatable by the control unit 130. An alignment of the probe 122' relative to the first observation plane 112 is thus determinable by evaluation of the image information of the first image recording device 104. This information about the alignment of the probe 122' can supplement the items of information provided by the motion sensor 125 and/or can be used as a start value. The system can be calibrated on the basis of this information.

Figure 3:
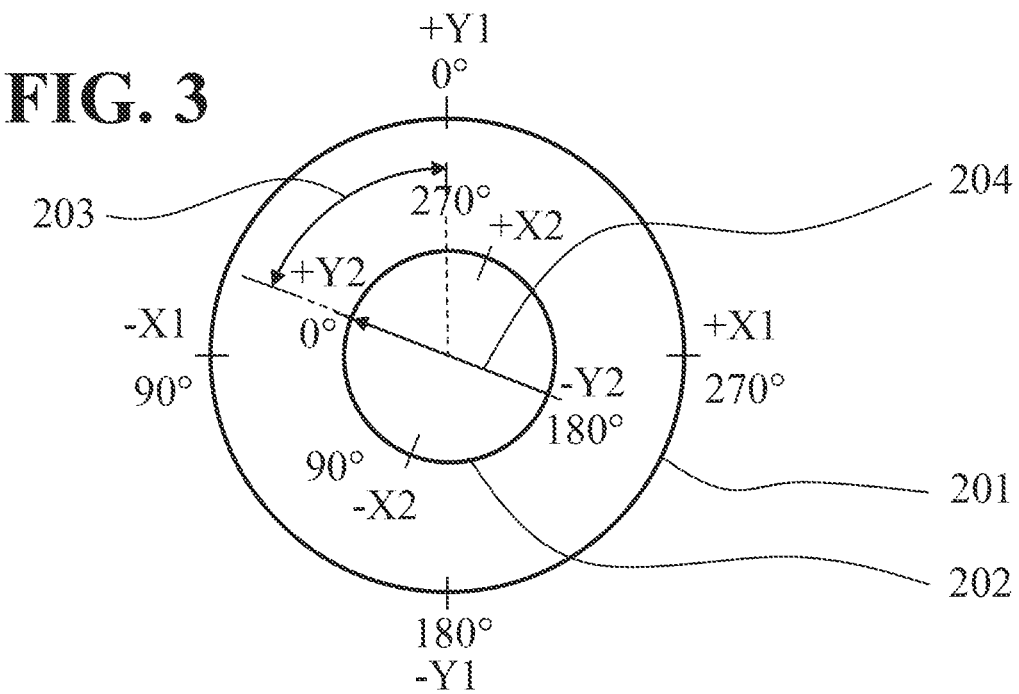
FIG. 3 shows a surgical microscope image together with an endoscope image.

FIG. 3 shows a surgical microscope image 201 together with an endoscope image 202. For explanation purposes, the endoscope image 202 is arranged at the center of the surgical microscope image 201. The surgical microscope image 201 in accordance with FIG. 3 corresponds to the surgical microscope image 152 in accordance with FIG. 2.

The first viewing direction of the observer relative to the first observation plane 112 is defined by the first viewing axis Y1. The second viewing direction of the endoscope is defined by the second viewing axis Y2.

The surgical microscope image 201 shows, in the Y1-direction or in the "0°" position, the first viewing direction toward the operation region 111, in a manner such as the latter can be viewed by the observer even without a surgical microscope in the first viewing direction along the first viewing axis Y1. The observer designates this "0°" position as "top".

By contrast, the endoscope image 202 is rotated by the angle 203. The second viewing axis Y2 of the endoscope image 202, which second viewing axis would be designated as "top" by the observer on account of the holding position of the endoscope, is thus arranged in a manner rotated by the angle 203, for example 70°, relative to the first viewing axis Y1 of the surgical microscope image 201.

Upon a rotation of the endoscope about the axis of the probe or upon a movement of the probe in the advance direction, i.e., in the axial direction of the axis of the probe, the represented image excerpt and/or the angle 203 of the endoscope image 202 change(s). Without information about said angle 203, the hand-eye coordination of the observer who is manually guiding the endoscope is hampered. This leads to vexation during movement of the endoscope and during assignment of the image contents.

Therefore, a graphical marking 204 is inserted in the represented second image, the endoscope image 202, said graphical marking indicating the direction of the second viewing axis Y2 in the second image. This graphical marking 204 is configured as a line with a direction arrow indicating the position and direction of the second viewing axis Y2. The observer can thus recognize very simply the relative orientation of the endoscope image 202 with respect to the viewing axis of the surgical microscope image 101. This facilitates guidance of the endoscope and hand-eye coordination for the observer.

The graphical marking 204 can be embodied in various geometric shapes and/or colors. The graphical marking 204 can be configured for example as a single arrow or a single line, a pin, a triangle or a line at the image edge. The graphical marking can be arranged at the upper or lower image edge or offset from the image edge, at the image center or at an arbitrary location in the image. The graphical marking 204 can be embodied in various suitable colors that contrast well in terms of color with the tissue being viewed, e.g., green or yellow. The colors can be freely selectable or fixedly preset. Even the exemplary embodiment as a short line segment at the image edge, along the second viewing axis Y2, may be sufficient. The line segment can have for example a length having an absolute value in a range of between 3% and 10% of the diameter of the endoscope image 202.

Figure 4:
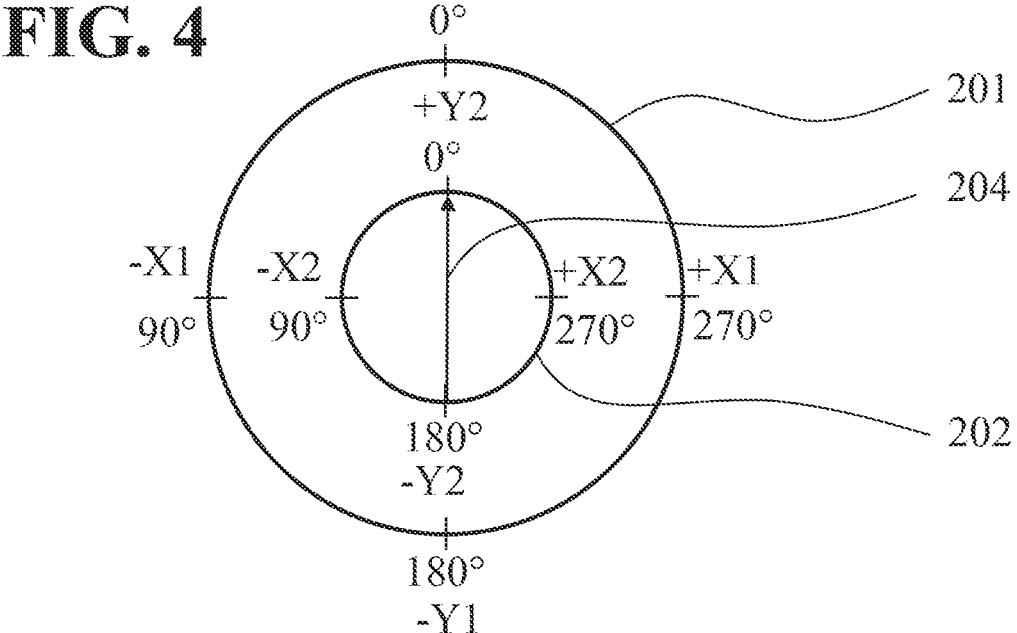
FIG. 4 shows the microscope image and the endoscope image in a mutually aligned arrangement.

FIG. 4 shows the microscope image 201 and the endoscope image 202 in accordance with FIG. 3 in a mutually aligned arrangement.

The endoscope image 202 is arranged in a manner rotated in the clockwise direction by the angle 203, which is 70° in this example, relative to the endoscope image 201, such that the second viewing axis Y2 of the endoscope image 202 corresponds to the first viewing axis Y1 of the microscope image 201.

The second orientation of the second image, the endoscope image 201, is thus aligned relatively to the first viewing axis Y1 depending on the angular position of the probe, the angle 203. As a result of the rotation of the endoscope image 202, the viewing and working direction of the endoscope now corresponds to that of the surgical microscope.

Since the motion sensor captures an angular position and/or angular change, which the control unit processes and evaluates, the alignment of the graphical marking 204 in the second image can be automatically tracked. This facilitates the hand-eye coordination of the observer holding the endoscope by hand and improves the handling of the endoscope.

In one exemplary embodiment, the first image recording device 104 is directly connected to the display device 140. In this case, the control unit 130 is connected only to the second image recording device 124 and the display device. Information about the orientation of the first viewing axis Y1 is stored in the control unit 130, such that the orientation of the second image is alignable relative to the viewing axis Y1 and/or the graphical marking 204 in the second image is alignable. The orientation of the second image and/or the graphical marking 204 are/is trackable depending on an angular position of the probe 122 relative to the first viewing axis Y1.

Figure 5:
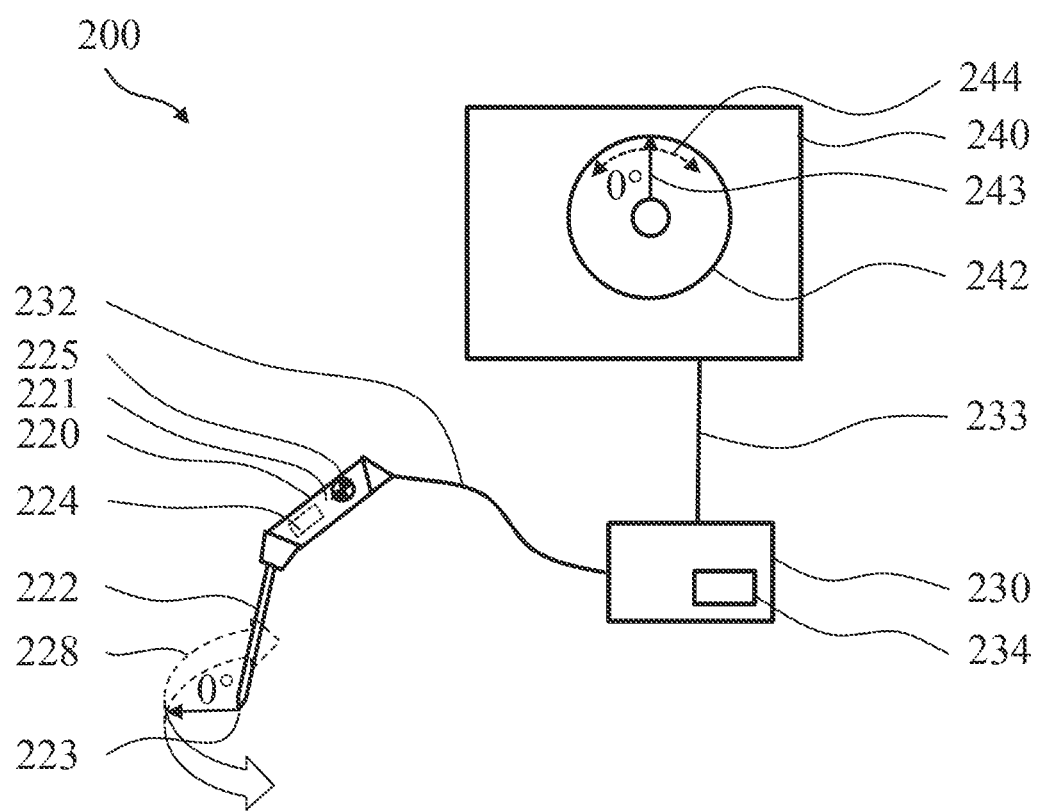
FIG. 5 shows the endoscope in accordance with FIG. 1 with a motion sensor and the insertion of a graphical marking on a display device.

FIG. 5 shows the endoscope in accordance with FIG. 1 with a motion sensor and the insertion of a graphical marking 204 on a display device 140.

The visualization system 200 has the same components as the visualization system in the operation scenario 100 in accordance with FIG. 1, with the reference signs being increased by 100. The illustration in FIG. 5 differs from the illustration in accordance with FIG. 1 in that it shows an endoscope 220 with a control unit 230 and a display device 240 without a surgical microscope.

The endoscope 220 comprises a probe 222 having a probe tip 223, a second image recording device 224, illustrated by dashed lines, and a motion sensor 225. The endoscope 220 is connected to the control unit 230 by a second line 232. The control unit 230 is coupled to the display device 240 via a third line 233. The control unit 230 comprises an image processing unit 234. The image recorded by the second image recording device 224 of the endoscope 220 is represented in a second image 242 on the display device 240. A graphical marking 243 indicates the second viewing direction Y2, or the "0°" position, of the endoscope 220. The graphical marking 243 is superimposed or inserted into the image communicated by the second image recording device 224 by means of the image processing unit 234.

Upon a rotation of the endoscope 220 about the center axis of the probe 222 toward the right or left, the viewing direction, or the "0°" position, of the endoscope 220 likewise changes toward the right or left. This rotational movement is represented by the semicircular first double-headed arrow 228. An angular change during this rotational movement is detected by the motion sensor 225 and communicated to the control unit 230. As a result, it is possible to calculate anew the representation of the second image 242, depending on the angular change of the endoscope 220, relative to the first viewing axis of the surgical microscope and to track the position of the graphical marking 243 anew in each case. The second image 242 represented by the image recording device 224 shows the viewing direction of the endoscope 220 and can be displayed together with the graphical marking 243 in two ways.

In a first representation variant, the second image 242 is displayed relative to the first viewing direction of the surgical microscope in such a way that the second viewing axis Y2 of the endoscope 220 corresponds to the first viewing axis Y1 of the microscope. In this case, the graphical marking 243 points in the same direction as the first viewing axis of the surgical microscope, for example, upward.

In a second representation variant, the second image 242 is displayed at a rotation angle relative to the first viewing direction of the surgical microscope, wherein the graphical marking 243 indicates the second viewing axis Y2 of the endoscope 220 relative to the first viewing axis Y1 of the surgical microscope. The graphical marking 243, representing the viewing direction, or the "0°" position, of the endoscope 220, is carried along synchronously with a rotational movement of the probe 222 of the endoscope 220 on the display device 240. This is illustrated by the second double-headed arrow 244.

In this way, an orientation relative to the images displayed on the display device 240 is possible very simply for the observer.

Figure 6:
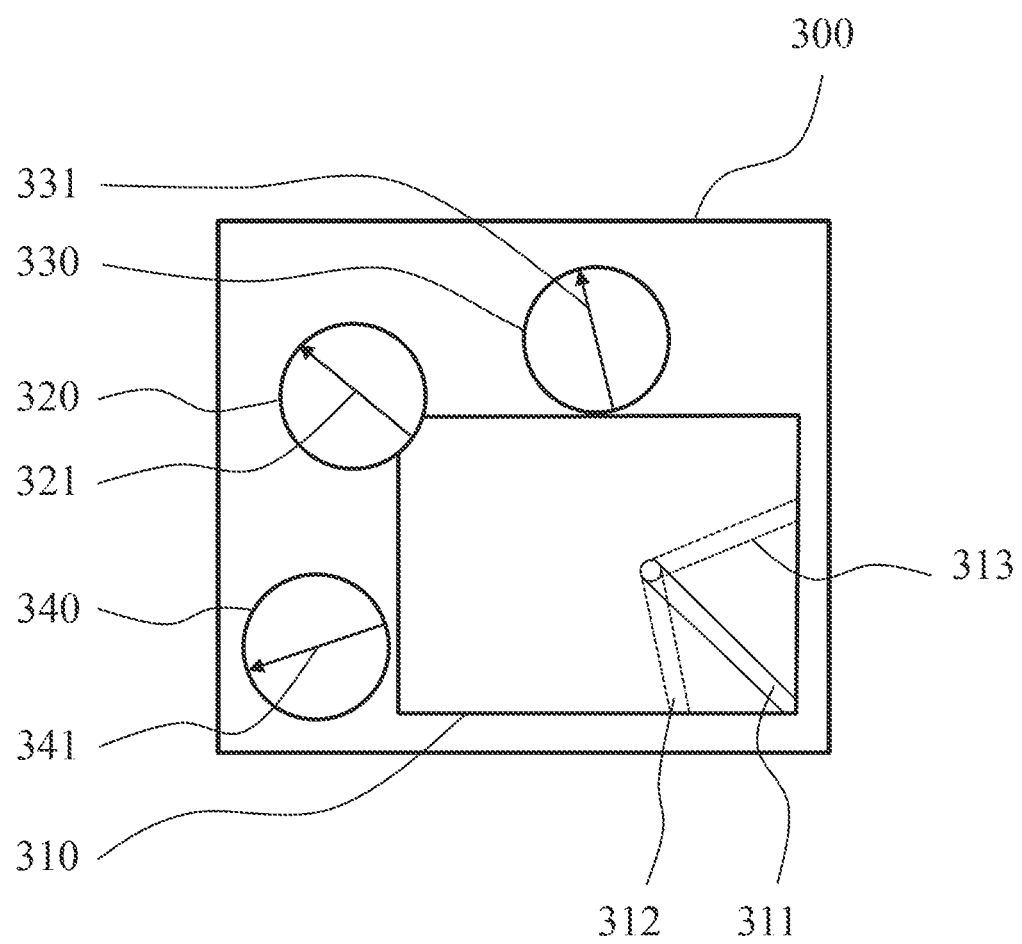
FIG. 6 shows a display device with one example of a Picture-in-Picture arrangement of a plurality of endoscope images with a graphical marking depending on the alignment of the viewing direction of the probe of the endoscope.

FIG. 6 shows a display device 300 with one example of a picture-in-picture arrangement of a plurality of endoscope images with a graphical marking depending on the alignment of the viewing direction of the probe of the endoscope.

The display device 300 shows a surgical microscope image, for example the representation of an operation site, in a rectangular first image 310. A first position of the probe 311 of an endoscope at a first point in time is visible in the surgical microscope image. The associated endoscope image at said first point in time is represented in a round second image 320. A second viewing axis of the endoscope, relative to the first viewing axis of the surgical microscope, is indicated by a first graphical marking 321.

An angular change to a second position of the probe 312 at a second point in time is captured by the motion sensor in the endoscope. The image captured at the second point in time is displayed in a round third image 330. A second graphical marking 331 shows the second viewing axis of the endoscope relative to the first viewing axis of the surgical microscope at said second point in time.

A further angular change to a third position of the probe 313 at a third point in time is captured by the motion sensor in the endoscope. The image captured at a third point in time is displayed in a round fourth image 340. A third graphical marking 341 shows the second viewing axis of the endoscope relative to the first viewing axis of the surgical microscope at said third point in time.

Figure 7:
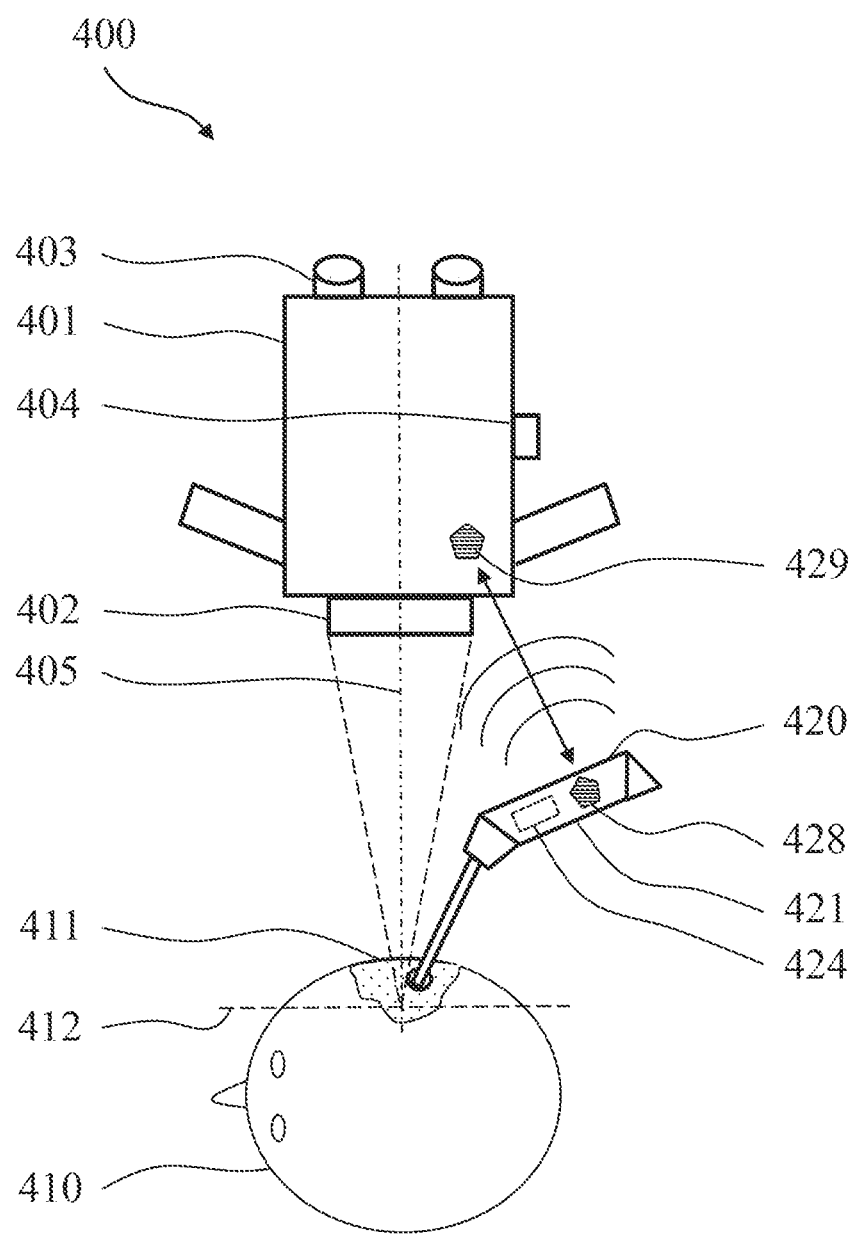
FIG. 7 shows a surgical microscope and an endoscope in an operation scenario with electromagnetic tracking of the probe according to a second exemplary embodiment of the disclosure.

FIG. 7 shows a surgical microscope and an endoscope in an operation scenario 400 with electromagnetic tracking of the probe according to a second exemplary embodiment of the disclosure.

The operation scenario 400 has a visualization system having the same components as the visualization system in the operation scenario 100 in accordance with FIG. 1, with the reference signs being increased by 300.

An endoscope 420 in accordance with FIG. 7 differs from the endoscope 120 in accordance with FIG. 1 in that the motion sensor 125 is replaced by a first electromagnetic tracking element 428.

The first electromagnetic tracking element 428 is related to a second electromagnetic tracking element 429 arranged on a surgical microscope 401. The first electromagnetic tracking element 428 and the second electromagnetic tracking element 429 can be formed by a transceiver pair. For this purpose, by way of example, an RFID chip or a solenoid can be arranged in a handpiece 421 of the endoscope. The distance between the handpiece 421 of the endoscope 420 and the surgical microscope 401 is in a favorable range for electromagnetic tracking. An arrangement of the first electromagnetic tracking element 428 within the handpiece 421 has the advantage that no outer tracking elements are arranged on the endoscope 420, which would hamper handling or have a disadvantageous effect on the view of the operation region 411. It is also conceivable for the first tracking element 428 and the second tracking element 429 to be detectable by an additional navigation system (not illustrated).

In another exemplary embodiment, both a first tracking element 428 and a motion sensor (not illustrated), for example a position or acceleration sensor, are arranged in the handpiece 421 of the endoscope 420. The combination of electromagnetic tracking and a motion sensor enables a very accurate motion and position detection of the endoscope 420.

In an exemplary embodiment of the disclosure in accordance with FIGS. 1 to 7, the visualization system comprises a first observation apparatus having a first image recording device 104, 404 for observing an operation region 111, 411 with a first observation plane 112, 412, wherein in the first observation plane 112, 412 viewing direction is defined by a first viewing axis Y1, and an endoscope 120, 220, 420 having a probe 122, 122', 222 and a second image recording device 124, 224, 424 for observing the operation region 111, 411 with a second observation plane 127 with a second viewing axis Y2.

The visualization system includes a display device 140, 240, 300, which represents a first image 141, 310 recorded by the first image recording device 104, 404 in a first orientation and a second image 142, 242, 320, 330, 340 recorded by the second image recording device 124, 224, 424 in a second orientation, and a control unit 130, 230, which is connected to the first image recording device 104, 404, the second image recording device 124, 224, 424 and the display device 140, 240, 300.

The endoscope 120, 220, 420 includes a motion sensor 125, 225, which is connected to the control unit 130, 230, an angular position of the probe 122, 122', 222 of the endoscope 120, 220, 420 in space being determinable by said motion sensor, where the control unit 130, 230 is configured to the effect that an angular position of the probe 122, 122', 222 of the endoscope 120, 220, 420 relative to the first viewing axis Y1 is determinable by evaluation of the data of the motion sensor 125, 225, such that the second orientation of the second image 142, 242, 320, 330, 340 is alignable depending on an angular position of the probe 122, 122', 222 relative to the first viewing axis Y1.

In one exemplary embodiment, a graphical marking 204, 321, 331, 341 is inserted in the second image 142, 242, 320, 330, 340 represented on the display device 140, 240, 300, said graphical marking indicating the direction of the second viewing axis Y2 in the second image 142, 242, 320, 330, 340, wherein the graphical marking 204, 321, 331, 341 is trackable depending on an angular position of the probe 122, 122', 222 relative to the first viewing axis Y1.

In one exemplary embodiment, the first observation apparatus is a surgical microscope 101, 401. The surgical microscope 101, 401 can be a conventional surgical microscope having eyepieces and at least one camera, or a purely digital, camera-based, surgical microscope.

In one exemplary embodiment, the first observation apparatus is a camera. The camera can be a commercially available camera or a camera with an additional optical unit.

According to a further exemplary embodiment of the disclosure, the endoscope can also be some other image capture device, for example a manually guided camera or an image capture device that can capture images based on ultrasound.

Figure 8:
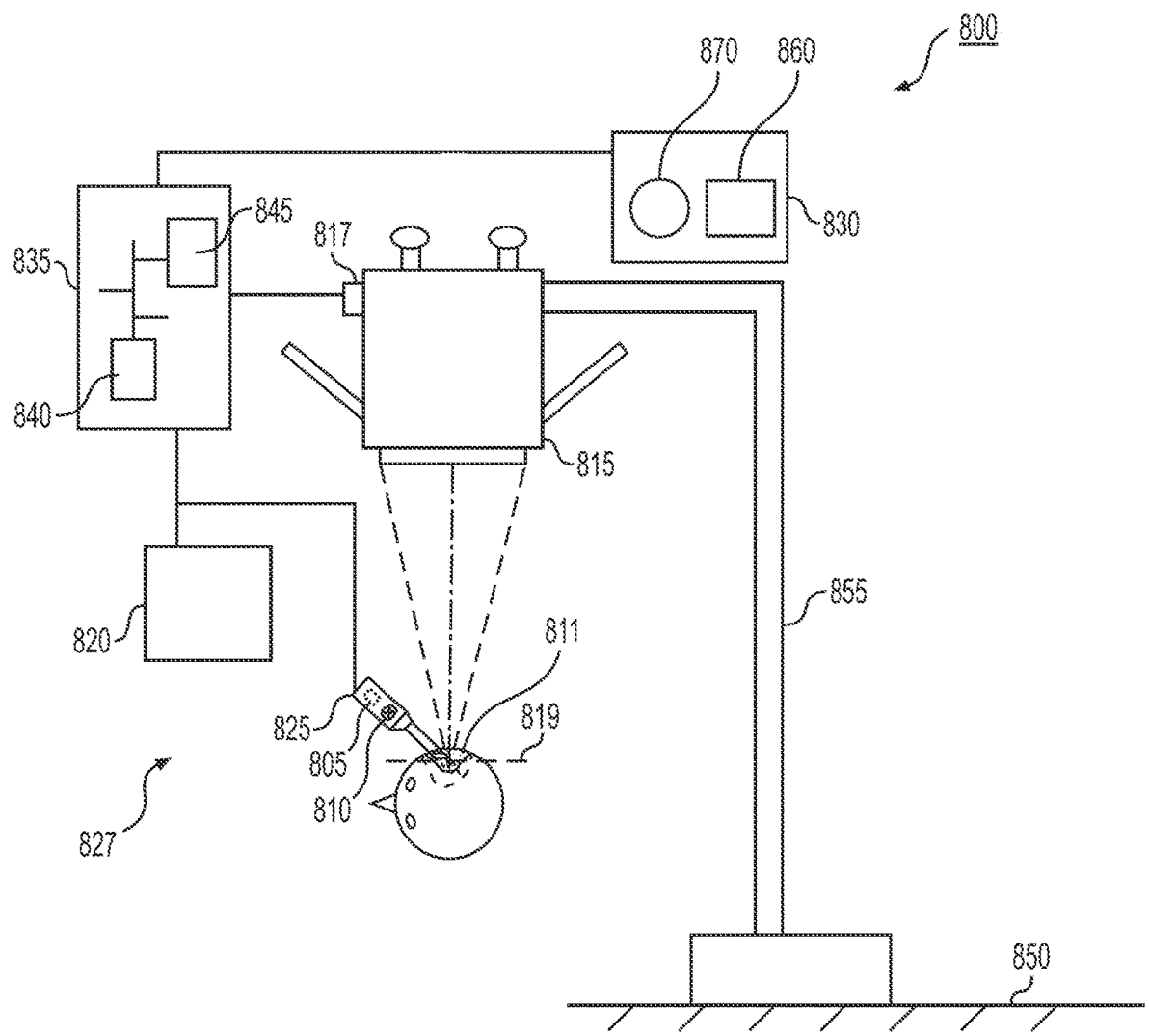
FIG. 8 shows a visualization system in an operation scenario according to a third exemplary embodiment of the disclosure.

Referring is now made to FIG. 8 (with continued reference to FIG. 2), which shows a visualization system 800 for operating an optical inspection tool 805 according to a third exemplary embodiment of the disclosure in an operation scenario.

The visualization system 800 includes an observation apparatus 815, an optical inspection tool 805, a display device 830, a floor stand 855, a tracking system 827, and a controller 835.

The observation apparatus 815 includes a first image recording device 817 which is configured to observe an operation region 811 at a first observation plane 819 and is movably mounted on the floor stand 855 via a suspension arm (not shown), for example. The first observation plane 819 has a first observation plane axis and a second observation plane axis and defines a first viewing axis which is perpendicular to the first plane axis and the second plane axis.

The optical inspection tool 805 includes a second image recording device 810 which is configured to observe the operation region 811 at a second observation plane 127 having a third plane axis and a fourth plane axis and defining a second viewing axis which is perpendicular to the third plane axis and the fourth plane axis.

The display device 830 is configured to represent at least one of a first image 860 recorded by the first image recording device 817 and a second image 870 recorded by the second image recording device 810. In other words, it is possible that only the second image 870 is represented on the display device 830.

The endoscope image (second image 870) needs to be displayed on the display device 830 in such a way that optimum hand-eye coordination is achieved when using the endoscope. That is because an incorrect orientation (rotation) of the endoscope image, i.e., of the second image 870 makes hand-eye coordination more difficult for the surgeon (not shown) and therefore leads to increased mental stress, risk of errors, and thus to an increased patient risk.

The display device 830 is typically ergonomically oriented towards the surgeon. Therefore, it is possible to automatically adjust the orientation (rotation) of the endoscope image i.e., the second image 870) to changing orientations of the endoscope (i.e., to the optical inspection tool 805) by determining a transformation of the endoscope image relative to the observation apparatus 815, for example, a microscope or microscope image (i.e., the first image 860), to ensure an optimal hand-eye coordination at all times.

The tracking system 827 includes a target detection device 820 and at least one target 825. As shown in FIG. 8, the tracking system 827 is integrated in the observation apparatus 815, i.e., in the surgical microscope. The tracking system 827 is configured to detect or determine an orientation of the optical inspection tool 805 relative to the observation apparatus 815. The information about the position and orientation of the optical inspection tool 805 can be utilized to determine the orientation of the second image 870 of the optical inspection tool 805 directly or indirectly relative to the microscope image, i.e., to the first image 860, or generally in space.

In addition, when the surgeon works with the observation apparatus 815, the surgeon configures and positions the observation apparatus 815 such that a good hand-eye coordination with the microscope image, i.e., the second image 860, is possible. Therefore, the position of the microscope, i.e., of the observation apparatus 815, can be used to infer the position of the surgeon relative to the observation apparatus 815. For example, the surgeon stands or sits in front of the observation apparatus 815 in such a way that her/his shoulder axis is aligned roughly parallel to an axis of the observation apparatus 815. A rotation of the observation apparatus 815 about this axis can be ignored because the surgeon does typically not adjust her/his position to this rotation.

The controller 835 includes a memory 840 and a processor 845 in communication with the display device 830, the first image recording device 817, the second image recording device 810, the tracking system 827, and the memory 840. According to another variant, the processor may only be in communication with the display device 830, the second image recording device 810, the tracking system 827, and the memory 840, e.g., in a configuration in which only the second image 870 is desired to be represented or displayed on the display device 830.

The processor 845 is configured to transform the second image 870 based on the orientation of the optical inspection tool 805 relative to the observation apparatus 815 or generally in space. Transformation can be achieved by rotating the second image 870 about the viewing axis of the second image 870 or by any other change in the orientation of the second image 870 in space, i.e., the transformation may include a plurality of degrees of freedom. In another variant, the processor 845 is configured to transform the second image 870 relative to the first image 860 based on the orientation of the optical inspection tool 805 relative to the observation apparatus 815 or generally in space.

The surgeon works with the observation apparatus, i.e., with the surgical microscope, and the optical inspection tool 805, i.e., the endoscope, in the operation region 811. The image 870 of the endoscope is displayed on a digital display device 830, e.g., on a monitor, as a data reflection in the eyepieces of the microscope 815, or in a head-mounted display (HMD) (not shown). However, the digital display device 830 is not limited thereto. Any other type of digital or non-digital display device is possible.

In a first variation, to transform the second image 870, the processor 845 is configured to generate a projected observation plane by projecting the second observation plane onto the first observation plane 819. The projected observation plane has a projected third plane axis and a projected fourth plane axis and defines a projected second viewing axis which is aligned perpendicular to the projected third plane axis and the projected fourth plane axis, and wherein the projected third plane axis, the projected fourth plane axis, and projected second viewing axis define a projected coordinate system. The processor is further configured to determine a rotation angle which indicates a rotation of the projected coordinate system about the projected second viewing axis such that the projected third plane axis is aligned parallel to and equally oriented with the first plane axis, and the projected fourth plane axis is aligned parallel to and equally oriented with the second plane axis, and to rotate the second image 870 about the rotation angle.

Figure 9:
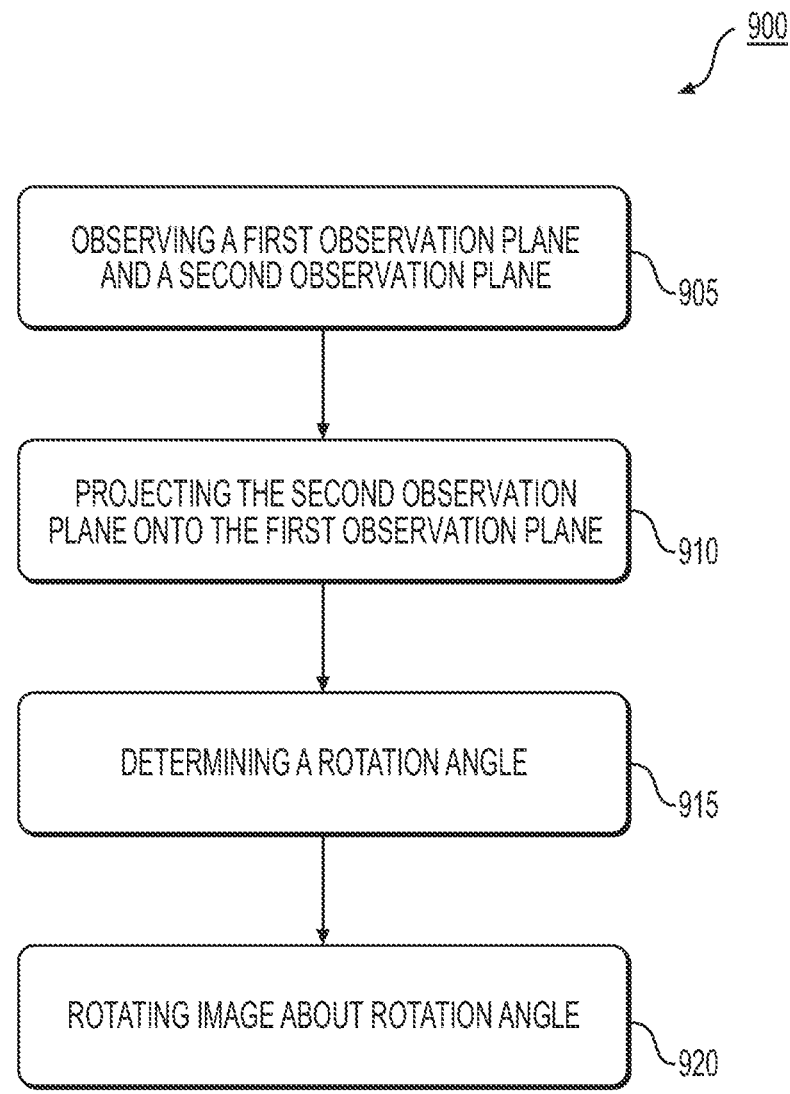
FIG. 9 shows a flowchart of a method according to an exemplary embodiment of the disclosure.

FIG. 9 shows a flowchart of a method 900 for operating an optical inspection tool 805 according to an exemplary embodiment of the disclosure. The method starts at step 905 at which the first observation plane 819 and the second observation plane 127 are observed. The first observation plane 819 has a first observation plane axis and a second observation plane axis and defines a first viewing axis which is perpendicular to the first plane axis and the second plane axis. The second observation plane 127 has a third plane axis and a fourth plane axis and defines a second viewing axis which is perpendicular to the third plane axis and the fourth plane axis. The method moves to step 910 at which the second observation plane 127 is projected onto the first observation plane 819 thereby generating a projected observation plane. The projected observation plane has a projected third plane axis and a projected fourth plane axis and defines a projected second viewing axis which is aligned perpendicular to the projected third plane axis and the projected fourth plane axis. The projected third plane axis, the projected fourth plane axis, and projected second viewing axis define a projected coordinate system. At step 915, a rotation angle is determined such that the projected third plane axis is aligned parallel to and equally oriented with the first plane axis, and the projected fourth plane axis is aligned parallel to and equally oriented with the second plane axis. At step 920, the second image 870 is rotated about the rotation angle.

To further explain the above transformation, a coordinate system of the first image 860 of the microscope can be denoted by K_M and a coordinate system of the second image 870 of the endoscope can be denoted by K_E. Relevant for the discussion are the respective coordinate axes x_E, y_E and x_M, y_M, as well as the perpendiculars to them z_E and z_M. Without limitation, the coordinate systems of the first image 860 and of the second image 870 are considered in this context. Downstream optics can exert a further rotation and/or translation on the considered coordinate system. However, since such rotations and/or translations are typically static in nature, they can be compensated by an additional transformation matrix.

The second image 870 is aligned or transformed according to the following steps: (1) the x_E/y_E plane is projected onto the x_M/y_M plane, (2) subsequently, the rotation of the projected coordinate system K_E' around the axis z_E' is determined such that the projected axes x_E are parallel to x_M and y_E are parallel to y_M. In addition to being parallel, the axis directions x_E to x_M and y_E to y_M must coincide, and (3) the display of the second image 870 on the display device 830 is rotated according to the determined angle.

If z_E is perpendicular to z_M, the following rule applies: An axis can always be projected into the K_M coordinate system and the above-described rules apply. For the second (perpendicular) axis, the rule applies that either top/bottom or right/left of the coordinate system K_M is taken over for the corresponding axis of the coordinate system K_E.

The above-described first variation is based on the assumption that only rotational changes may be made to the second image 870 (in order not to alienate the image content). Should this restriction not exist, the above projection can also contain more degrees of freedom.

To transform the second image 870, the processor is further configured to define a reference plane 850. The reference plane 850 is a plane having a first reference plane axis and a second reference plane axis. The first and second reference plane axes are aligned perpendicular to the gravitation or gravitational force.

Figure 11:
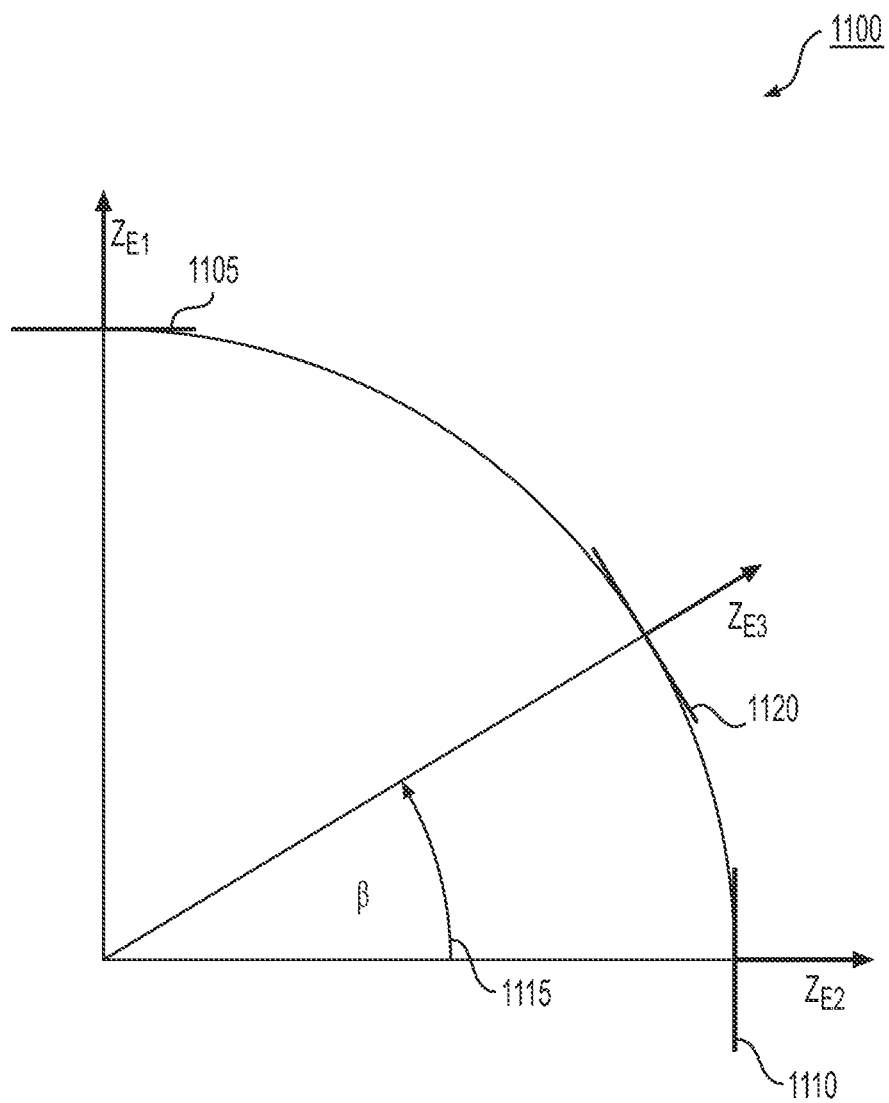
FIG. 11 shows orientations of projected observation planes of an optical inspection tool for various tilt angles.

Referring now to FIG. 11 (with continued reference to FIG. 8). FIG. 11 shows orientations of projected observation planes of the optical inspection tool 805 for various tilt angles β labelled with reference numeral 1115. Specifically, as shown in FIG. 11, plane 1105 is a horizontal plane and plane 1110 is a vertical plane. Plane 1120 is a plane rotated about the tilt angle β and the tilt angle β indicates a deviation from the horizontal plane 1105.

In a second variation, to transform the second image 870, the processor 845 is configured to define the horizontal plane 1105 and the vertical plane 1110, wherein the horizontal plane 1105 is aligned parallel to and equally oriented with the reference plane 850, and the vertical plane 1110 is aligned perpendicular to the reference plane 850. The processor 845 is further configured to generate a projected horizontal observation plane by projecting the second observation plane onto the horizontal plane 1105 and a projected vertical observation plane by projecting the second observation plane onto the vertical observation plane 1110, to determine a first rotation angle $\alpha_1$ such that a rotated third plane axis of the rotated second observation plane is aligned parallel to and equally oriented with the projected first plane axis, and to determine a second rotation angle $\alpha_2$ such that a rotated fourth plane axis of the rotated second observation plane is directed away from the reference plane 850, to determine the tilt angle β relative to the reference plane 850, to determine a third rotation angle $\alpha_3$ based on the first rotation angle $\alpha_1$, the second rotation angle $\alpha_2$, and the tilt angle β, and to rotate the second image 870 about the third rotation angle $\alpha_3$.

Figure 10:
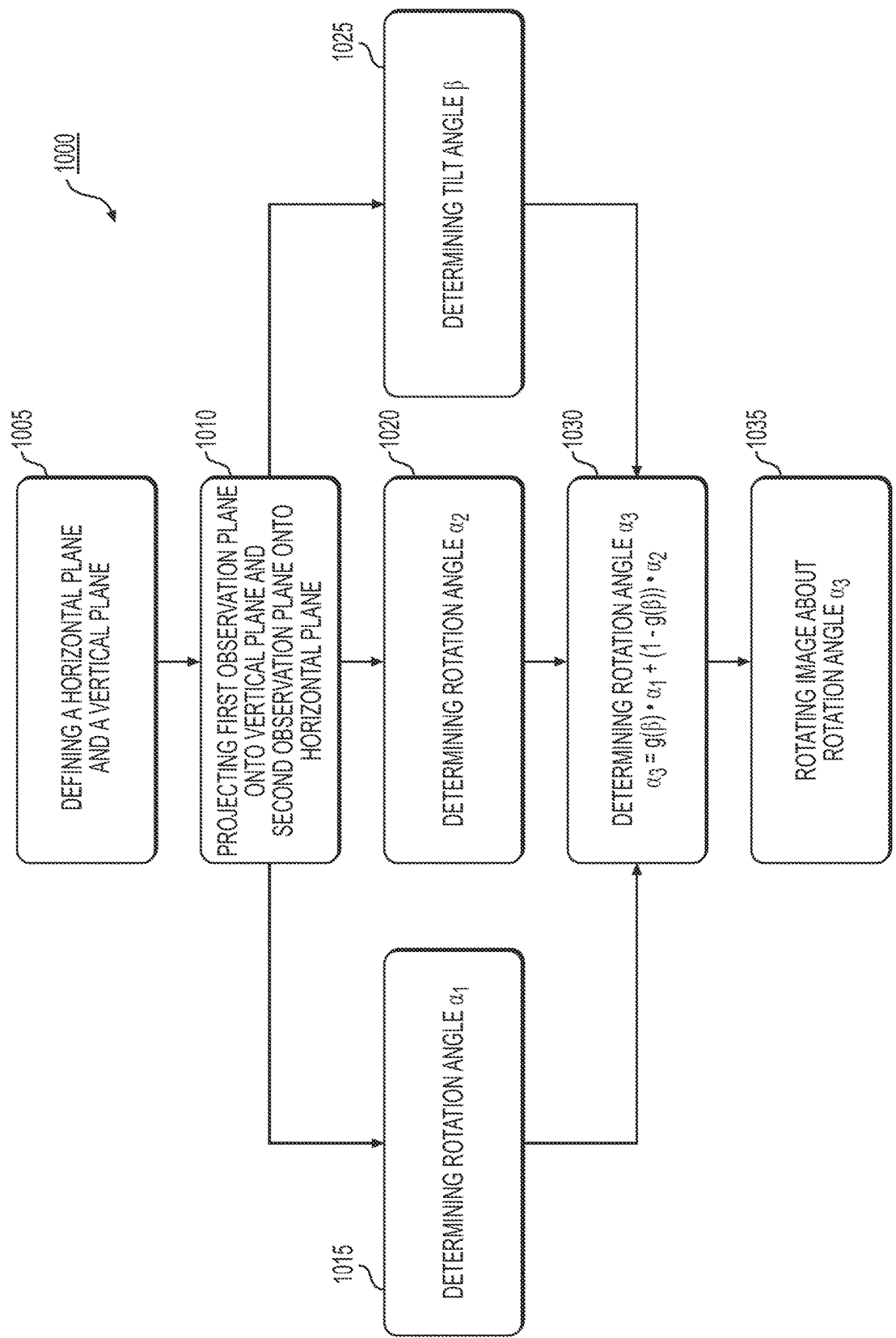
FIG. 10 shows a flowchart of a method according to another exemplary embodiment of the disclosure.

FIG. 10 shows a flowchart of a method 1000 for operating an optical inspection tool 805 according to another exemplary embodiment of the disclosure. The method 1000 starts at step 1005 at which a horizontal plane 1105 and the vertical plane 1110 are defined. The horizontal plane 1105 is aligned parallel to and equally oriented with the reference plane 850 and the vertical plane 1110 is aligned perpendicular to the reference plane 850.

The method continues to step 1010 at which the first observation plane 819 is projected onto the horizontal plane 1105 and the second observation plane 127 is projected onto the vertical observation plane 1110. The first observation plane 819 has a first observation plane axis and a second observation plane axis and defines a first viewing axis which is perpendicular to the first plane axis and the second plane axis. The second observation plane 127 has a third plane axis and a fourth plane axis and defines a second viewing axis which is perpendicular to the third plane axis and the fourth plane axis.

In step 1015, a first rotation angle $\alpha_1$ is determined such that a rotated third plane axis of the rotated second observation plane is aligned parallel to and equally oriented with the projected first plane axis. In step 1020, a second rotation angle $\alpha_2$ is determined such that a rotated fourth plane axis of the rotated second observation plane is directed away from the reference plane 850. In step 1025, a tilt angle β 1115 is determined relative to the reference plane 850, and in step 1030, a rotation angle $\alpha_3$ is determined in accordance with $$\alpha_3 = g(\beta) \cdot \alpha_1 + (1 - g(\beta)) \cdot \alpha_2$$

wherein $\alpha_1$ is the first rotation angle, $\alpha_2$ is the second rotation angle, and $g(\beta)$ is a transition function of the tilt angle β.

The method 1000 continues to step 1035 at which the second image 870 is rotated about the third rotation angle $\alpha_3$.

The above method 1000 can also be described in terms of the above-mentioned coordinate system K_M of the first image 860 of the microscope and the coordinate system K_E of the second image 870 of the endoscope with two special cases and a general case.

The first special case applies when z_E is perpendicular to the reference plane 850 (e.g., the floor), the second image 870 on the display device 830 is rotated about the rotation angle $\alpha_1$ such that the axis x_E' of the rotated image is parallel and equally oriented as the axis x_M' projected on the reference plane 850. This ensures that a movement of the optical inspection tool 805 away from the observer is an upward movement in the second image 870.

The second special case applies when z_E is parallel to the reference plane 850. In this case, the second image 870 on the display device 830 is rotated about the rotation angle $\alpha_2$ such that the axis y_E' of the rotated image points upwards. This ensures that an upward movement of the optical inspection tool 805 is an upward movement in the second image 870.

For cases between the first and second special cases, the general case applies. In the general case, the rotation angle $\alpha_3$ is determined based on a first rotation angle $\alpha_1$ and a second rotation angle $\alpha_2$ and with a transition function $g(\beta)$, i.e., as a function of the deviation from the horizontal plane.

The second image 870 is first projected onto a vertical plane 1110 and a horizontal plane 1105. Subsequently, the two rotation angles $\alpha_1$ and $\alpha_2$ are determined for the two special cases as described above.

Thereafter, the third rotation angle $\alpha_3$ is determined in accordance with $$\alpha_3 = g(\beta) \cdot \alpha_1 + (1 - g(\beta)) \cdot \alpha_2$$

wherein $\alpha_1$ is the first rotation angle, $\alpha_2$ is the second rotation angle, and $g(\beta)$ is a transition function of the tilt angle β.

According to an exemplary embodiment of the disclosure, a value of a function $g(\beta)$ of the tilt angle β is 0 when the tilt angle β is 0°, the value of the function $g(\beta)$ of the tilt angle β is 1 when the tilt angle β is 90°, the function $g(\beta)$ of the tilt angle β is monotonically increasing, and the function $g(\beta)$ of the tilt angle β is adjustable.

According to another exemplary embodiment of the disclosure, the target detection device 820 is a camera, and the at least one target is a marker. The marker can be, e.g., a matrix barcode but is not limited thereto. Any other marker, such as for example reflective markers or position markers provided by Brainlab AG are also possible.

According to yet another exemplary embodiment of the disclosure, the second image 870 is transformed relative to the first image 860 by training the visualization system 800. To transform the second image 870 relative to the first image 860 by training, the second image 870 is repeatedly manually rotated about the projected second viewing axis corresponding to a rotation angle depending on the orientation of the optical inspection tool 805 relative to the observation apparatus 815. According to this exemplary embodiment of the disclosure, the processor is further configured to store values of the rotation angle in a training database (which can be stored in memory 840) each time the second image 870 is rotated about the rotation angle, to compare the values previously stored in the training database with the values subsequently stored in the training database, and to automatically rotate the second image 870 about the rotation angle based on the training of the visualization system.

In other words, the image is initially rotated either according to one of the variations discussed above or it is not at all automatically rotated. Thus, in this case, the observer is left with the option to rotate the second image 870 manually.

A self-learning system learns the rotations, or the corrections of the observer's rotations as follows. Each time the observer rotates the image manually, a new training data set is generated. Once sufficient validity of the training data has been established (checked by matching the learned rotations with newly made adjustments), the learned procedure is used for an adjusted automatic correction.

In general, either the data of only one observer or the data of a group of observers (locally or globally) can be used for transforming the second image 870 relative to the first image 860 by training or learning. In addition, the observer can access learned procedures from other observers (e.g., chief physicians, etc.).

Figure 12:
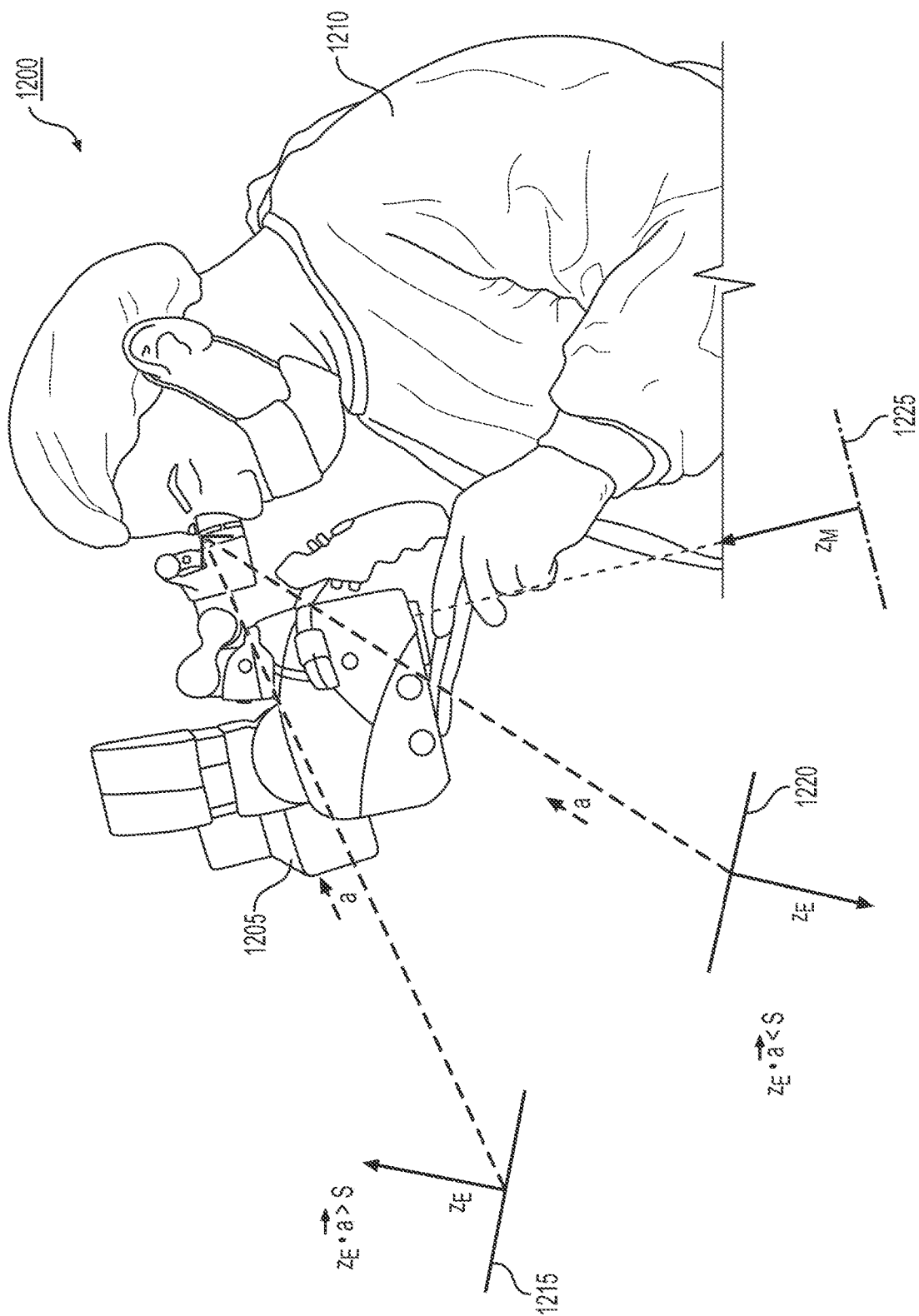
FIG. 12 illustrates an operation scenario in which a transformation of an image of the optical inspection tool by inversion is provided according to an exemplary embodiment of the disclosure.

Reference is now made to FIG. 12 which illustrates an operation scenario 1200 in which a transformation of the second image 870 of the optical inspection tool 805 by inversion is provided according to a further an exemplary embodiment of the disclosure.

This procedure is necessary in rare cases where the second image 870 is oriented in such a way that the observer sees it from "behind," e.g., in the case of an approach from behind or from below, the orientations of the X axes are reversed. Thus, when the observer 1210 moves the optical inspection tool 805 to the right when viewed from the front, it moves to the left in the second image 870. In order to relieve the observer cognitively, the X-axis of the image can also be automatically inverted, mirrored or reflected after rotation, such that left and right are swapped in the image.

The second image 870 can also be reflected by calculating a scalar product of Z_E of the image planes 1215 and 1220 of the optical inspection tool 805 and Z_M of the image plane 1225 of the observation apparatus 815, or, alternatively, an imaginary axis a between the coordinate system of the optical inspection tool 805 and a part of the observation apparatus 815 (e.g., the eyepieces as a rough approximation of the surgeon's position) can be defined. In response to a certain negative threshold value S, in FIG. 12, the image plane 1220 is automatically inverted relative to image plane 1215.

According to another variant, it is also possible to transform the second image 870 by defining a vertical axis of the second image 870 and reflecting the second image 870 on the vertical axis.

The term "comprising" (and its grammatical variations) as used herein is used in the inclusive meaning of "having" or "including" and not in the exclusive sense of "consisting only of." The terms "a" and "the" as used herein are understood to encompass the plural as well as the singular.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

100, 400, 1200 Operation scenario
101, 401 Surgical microscope
102, 402 Main objective
103, 403 Eyepieces
104, 404, 817 First image recording device
105, 405 Optical axis
110, 410 Object to be observed
111, 411, 811 Operation region
112, 412, 819 First observation plane
113, 113' Body opening
120, 220, 420 Endoscope
121, 421 Handpiece
122, 122', 222 Probe
123, 223 Probe tip
124, 224, 424, 810 Second image recording device
125, 225 Motion sensor
126 Aperture angle
127 Second observation plane
130, 230 Control unit
131 First line
132, 232 Second line
133, 233 Third line
134, 234 Image processing unit
140, 240, 830 Display device
141, 860 First image
142, 242, 870 Second image
150 First coordinate system
151 First coordinate system
152 Surgical microscope image
160 Second coordinate system
200 Visualization system
201 Surgical microscope image
202 Endoscope image
203 Angle
204 Graphical marking
228 First double-headed arrow
243 Graphical marking
244 Second double-headed arrow
300 Display device
310 First image
311 First position of the probe
312 Second position of the probe
313 Third position of the probe
320 Second image
321 First graphical marking
330 Third image
331 Second graphical marking
340 Fourth image
341 Third graphical marking
428 First electromagnetic tracking element
429 Second electromagnetic tracking element
800 Visualization system
805 Optical inspection tool
815 Observation apparatus
820 Target detection device
825 Target
827 Tracking system
835 Controller
840 Memory
845 Processor
850 Reference plane
855 Floor stand
1210 Observer, surgeon
1215, 1220, 1225 Image plane

What is claimed is:
1. A visualization system for operating an optical inspection tool, the visualization system comprising:
an observation apparatus having a first image recording device configured to observe an operation region at a first observation plane having a first observation plane axis and a second observation plane axis and defining a first viewing axis which is perpendicular to the first observation plane axis and the second observation plane axis;

the optical inspection tool having a second image recording device configured to observe the operation region at a second observation plane having a third observation plane axis and a fourth observation plane axis and defining a second viewing axis which is perpendicular to the third observation plane axis and the fourth observation plane axis;

a display device configured to represent at least one of a first image recorded by the first image recording device and a second image recorded by the second image recording device;

a tracking system including a target detection device and at least one target and being configured to determine an orientation of the optical inspection tool relative to the observation apparatus;

a controller including a memory and a processor in communication with the display device, the first image recording device, the second image recording device, the tracking system, and the memory; and the processor being configured to transform the second image based on the orientation of the optical inspection tool relative to the observation apparatus, wherein to transform the second image, the processor is further configured to:

generate a projected observation plane by projecting the second observation plane onto the first observation plane, wherein the projected observation plane has a projected third observation plane axis and a projected fourth observation plane axis and defines a projected second viewing axis which is aligned perpendicular to the projected third observation plane axis and the projected fourth observation plane axis, and wherein the projected third observation plane axis, the projected fourth observation plane axis, and projected second viewing axis define a projected coordinate system;

determine a rotation angle which indicates a rotation of the projected coordinate system about the projected second viewing axis such that the projected third observation plane axis is aligned parallel to and equally oriented with the first observation plane axis, and the projected fourth observation plane axis is aligned parallel to and equally oriented with the second observation plane axis; and rotate the second image about the rotation angle about the projected second viewing axis.

2. The visualization system of claim 1, wherein:
the observation apparatus is a microscope,
the optical inspection tool is an endoscope,
the target detection device is a camera, and
the at least one target is a marker.

3. The visualization system of claim 1, wherein to transform the second image, the processor is further configured to:
define a vertical axis of the second image; and
reflect the second image on the vertical axis.

4. The visualization system of claim 1, wherein:
the second image is transformed by training the visualization system, and
to transform the second image relative to the first image by training:
the second image is repeatedly manually rotated about the second viewing axis corresponding to a rotation angle depending on the orientation of the optical inspection tool relative to the observation apparatus; and the processor is further configured to:
store values of the rotation angle in a training database each time the second image is rotated about the rotation angle;
compare the values previously stored in the training database with the values subsequently stored in the training database; and
automatically rotate the second image about the rotation angle based on the training of the visualization system.

5. A visualization system for operating an optical inspection tool, the visualization system comprising:
an observation apparatus having a first image recording device configured to observe an operation region at a first observation plane having a first observation plane axis and a second observation plane axis and defining a first viewing axis which is perpendicular to the first observation plane axis and the second observation plane axis;

the optical inspection tool having a second image recording device configured to observe the operation region at a second observation plane having a third observation plane axis and a fourth observation plane axis and defining a second viewing axis which is perpendicular to the third observation plane axis and the fourth observation plane axis;

a display device configured to represent at least one of a first image recorded by the first image recording device and a second image recorded by the second image recording device;

a tracking system including a target detection device and at least one target and being configured to determine an orientation of the optical inspection tool relative to the observation apparatus;

a controller including a memory and a processor in communication with the display device, the first image recording device, the second image recording device, the tracking system, and the memory; and the processor being configured to transform the second image based on the orientation of the optical inspection tool relative to the observation apparatus, wherein:
to transform the second image, the processor is further configured to;
define a reference plane,
generate a projected first observation plane by projecting the first observation plane onto the reference plane, wherein the projected first observation plane has a projected first observation plane axis and a projected second observation plane axis and defines a projected first viewing axis; and
when the second viewing axis is aligned perpendicular to the reference plane, determine a first rotation angle $\alpha_1$ and rotate the second image about the first rotation angle $\alpha_1$ about the projected second viewing axis such that a rotated third observation plane axis of the rotated second observation plane is aligned parallel to and equally oriented with the projected first observation plane axis, and the projected fourth observation plane axis is aligned parallel to and equally oriented with the second observation plane axis, wherein the reference plane is a plane having a first reference plane axis and a second reference plane axis, and wherein the first and second reference plane axes are aligned perpendicular to a gravity.

6. The visualization system of claim 5, wherein to transform the second image, the processor is further configured to:
define a horizontal plane and a vertical plane, wherein the horizontal plane is aligned parallel to the reference plane and the vertical plane is aligned perpendicular to the reference plane;
generate a projected horizontal observation plane by projecting the second observation plane onto the horizontal plane and a projected vertical observation plane by projecting the second observation plane onto the vertical observation plane;
determine a first rotation angle $\alpha_1$ such that a rotated projected third observation plane axis of the projected horizontal observation plane is aligned parallel to and equally oriented with the projected first observation plane axis;
determine a second rotation angle $\alpha_2$ such that a rotated projected fourth observation plane axis of the projected vertical observation plane is directed away from and perpendicular to the reference plane in a direction opposite to the gravity;
determine a tilt angle $\beta$ relative to the reference plane;
determine a third rotation angle $\alpha_3$ based on the first rotation angle $\alpha_1$, the second rotation angle $\alpha_2$, and the tilt angle $\beta$; and
rotate the second image about the third rotation angle $\alpha_3$ about the projected second viewing axis.

7. The visualization system of claim 6, wherein the third rotation angle $\alpha_3$ is determined in accordance with $$\alpha_3 = g(\beta)\cdot\alpha_1 + (1-g(\beta))\cdot\alpha_2, \text{ and}$$

wherein $\alpha_1$ is the first rotation angle, $\alpha_2$ is the second rotation angle, and $g(\beta)$ is a function of the tilt angle $\beta$.

8. The visualization system of claim 7, wherein:
a value of the function $g(\beta)$ of the tilt angle $\beta$ is 0 when the tilt angle $\beta$ is 0°,
the value of the function $g(\beta)$ of the tilt angle $\beta$ is 1 when the tilt angle $\beta$ is 90°,
the function $g(\beta)$ of the tilt angle $\beta$ is monotonically increasing, and
the function $g(\beta)$ of the tilt angle $\beta$ is adjustable.

9. A method for operating an optical inspection tool, the method comprising:
observing, with an observation apparatus, an operation region at the first observation plane, the first observation plane having a first observation plane axis and a second observation plane axis and defining a first viewing axis which is aligned perpendicular to the first observation plane axis and the second observation plane axis;
observing, with the optical inspection tool, the operation region at the second observation plane, the second observation plane having a third observation plane axis and a fourth observation plane axis and defining a second viewing axis which is aligned perpendicular to the third observation plane axis and the fourth observation plane axis;
representing at least one of a first image recorded by a first image recording device and a second image recorded by a second image recording device;
determining, with a tracking system, an orientation of the optical inspection tool relative to the observation apparatus; and transforming the second image based on the orientation of the optical inspection tool relative to the observation apparatus, wherein transforming the second image comprises:
generating a projected observation plane by projecting the second observation plane onto the first observation plane, wherein the projected observation plane has a projected third observation plane axis and a projected fourth observation plane axis and defining a projected second viewing axis which is aligned perpendicular to the projected third observation plane axis and the projected fourth observation plane axis, and wherein the projected third observation plane axis, the projected fourth observation plane axis, and projected second viewing axis define a projected coordinate system;
determining a rotation angle which indicates a rotation of the projected coordinate system about the projected second viewing axis such that the projected third observation plane axis is aligned parallel to and equally oriented with the first observation plane axis, and the projected fourth observation plane axis is aligned parallel to and equally oriented with the second observation plane axis; and
rotating the second image about the rotation angle about the projected second viewing axis.

10. The method of claim 9, wherein:
transforming the second image comprises defining a reference plane,
the reference plane is a plane having a first reference plane axis and a second reference plane axis, and
the first and second reference plane axes are aligned perpendicular to a gravity.

11. The method of claim 10, wherein transforming the second image comprises:
generating a projected first observation plane by projecting the first observation plane onto the reference plane, wherein the projected first observation plane has a projected first observation plane axis and a projected second observation plane axis and defines a projected first viewing axis; and
when the second viewing axis is aligned perpendicular to the reference plane, determining a first rotation angle $\alpha_1$ and rotating the second image about the first rotation angle $\alpha_1$ such that a rotated third observation plane axis of the rotated second observation plane is aligned parallel to and equally oriented with the projected first observation plane axis, and the projected fourth observation plane axis is aligned parallel to and equally oriented with the second observation plane axis.

12. The method of claim 10, wherein transforming the second image comprises:
defining a horizontal plane and a vertical plane, wherein the horizontal plane is aligned parallel to and equally oriented with the reference plane and the vertical plane is aligned perpendicular to the reference plane;
generating a projected horizontal observation plane by projecting the second observation plane onto the horizontal plane and generating a projected vertical observation plane by projecting the second observation plane onto the vertical observation plane;
determining a first rotation angle $\alpha_1$ such that a rotated projected third observation plane axis of the projected horizontal observation plane is aligned parallel to and equally oriented with the projected first observation plane axis;

determining a second rotation angle $\alpha_2$ such that a rotated projected fourth observation plane axis of the projected vertical observation plane is directed away from and perpendicular to the reference plane in a direction opposite to the gravity;

determining a tilt angle $\beta$ relative to the reference plane;

determining a third rotation angle $\alpha_3$ based on the first rotation angle $\alpha_1$, the second rotation angle $\alpha_2$, and the tilt angle $\beta$; and rotating the second image about the third rotation angle $\alpha_3$ about the projected second viewing axis.

13. The method of claim 12, wherein the third rotation angle $\alpha_3$ is determined in accordance with $$\alpha_3 = g(\beta) \cdot \alpha_1 + (1 - g(\beta)) \cdot \alpha_2, \text{ and}$$

wherein $\alpha_1$ is the first rotation angle, $\alpha_2$ is the second rotation angle, and $g(\beta)$ is a function of the tilt angle $\beta$.

14. The method of claim 13, wherein:
a value of a function $g(\beta)$ of the tilt angle $\beta$ is 0 when the tilt angle $\beta$ is 0°,
the value of the function $g(\beta)$ of the tilt angle $\beta$ is 1 when the tilt angle $\beta$ is 90°,
the function $g(\beta)$ of the tilt angle $\beta$ is monotonically increasing, and
the function $g(\beta)$ of the tilt angle $\beta$ is adjustable.

15. The method of claim 9, wherein:
the observation apparatus is a microscope,
the optical inspection tool is an endoscope,
the target detection device is a camera, and
the at least one target is a marker.

16. The method of claim 9, wherein transforming the second image comprises:
defining a vertical axis of the second image; and
reflecting the second image on the vertical axis.

17. The method of claim 9, further comprising:
transforming the second image by training the visualization system, and
to transform the second image by training:
repeatedly manually rotating the second image about the projected second viewing axis corresponding to a rotation angle depending on the orientation of the optical inspection tool relative to the observation apparatus;
storing values of the rotation angle in a training database each time the second image is rotated about the rotation angle;
comparing the values previously stored in the training database with the values subsequently stored in the training database; and
automatically rotating the second image about the rotation angle based on the training of the visualization system.

* * * * *

UNITED STATES PATENT AND TRADEMARK OFFICE
CERTIFICATE OF CORRECTION

PATENT NO. : 12,262,866 B2
APPLICATION NO. : 17/508865
DATED : April 1, 2025
INVENTOR(S) : Christian Voigt et al.

Page 1 of 1

It is certified that error appears in the above-identified patent and that said Letters Patent is hereby corrected as shown below:

In the Claims

<u>In Column 31, Claim 6:</u>
Line 24: Delete "the" before "gravity"

<u>In Column 33, Claim 12:</u>
Line 5: Delete "the" before "gravity"

Signed and Sealed this
Second Day of September, 2025

Coke Morgan Stewart
*Acting Director of the United States Patent and Trademark Office*